US007325485B2

(12) United States Patent
Carhuff et al.

(10) Patent No.: US 7,325,485 B2
(45) Date of Patent: Feb. 5, 2008

(54) CLEAN-IN-PLACE AUTOMATED FOOD OR BEVERAGE DISPENSER

(75) Inventors: Peter W. Carhuff, Eau Claire, WI (US); Takeshi Masu, Ridgefield, CT (US); Gene Clyde, New Milford, CT (US); Edward L. Dickinson, Littleton, MA (US); Andrew C. Harvey, Waltham, MA (US); Edward M. Kolvek, West Newbury, MA (US); Michael H. Lago, New Milford, CT (US)

(73) Assignee: Nestec S.A., Vevey (CH)

( * ) Notice: Subject to any disclaimer, the term of this patent is extended or adjusted under 35 U.S.C. 154(b) by 249 days.

(21) Appl. No.: 11/033,867

(22) Filed: Jan. 13, 2005

(65) Prior Publication Data
US 2005/0115597 A1 Jun. 2, 2005

Related U.S. Application Data

(63) Continuation of application No. 10/328,826, filed on Dec. 24, 2002, now Pat. No. 6,889,603.

(51) Int. Cl.
*A47J 31/00* (2006.01)
(52) U.S. Cl. ............................ 99/452; 99/453; 99/468; 99/483; 134/169 R
(58) Field of Classification Search ................. 99/452, 99/453, 468, 483, 456, 457; 134/169 R, 134/166 R, 95.1; 137/240
See application file for complete search history.

(56) References Cited

U.S. PATENT DOCUMENTS

| 4,465,210 A | 8/1984 | Iwanami ..................... 222/148 |
| 4,848,381 A | 7/1989 | Livingston et al. ........... 134/57 |
| 5,503,064 A | 4/1996 | Scheel et al. ................. 99/453 |
| 5,783,245 A | 7/1998 | Simpson, II ................ 426/580 |
| 5,799,832 A | 9/1998 | Mayo .......................... 222/135 |
| 5,855,295 A | 1/1999 | Lee ............................... 222/1 |
| 6,024,252 A | 2/2000 | Clyde .......................... 222/105 |
| 6,161,558 A | 12/2000 | Franks et al. ................. 134/57 |
| 6,240,952 B1 | 6/2001 | Schroeder ................... 137/240 |
| 6,287,515 B1 | 9/2001 | Koosman et al. ............. 422/22 |
| 6,446,659 B2 | 9/2002 | Schroeder ................... 137/240 |

(Continued)

FOREIGN PATENT DOCUMENTS

DE 199 55 195 A1 5/2001

(Continued)

*Primary Examiner*—Reginald L. Alexander
(74) *Attorney, Agent, or Firm*—Winston & Strawn LLP

(57) ABSTRACT

The invention relates to an automated food product dispenser comprising an interface connection configured to establish a supply of a milk-based fluid from a reservoir (for example, a container or a bag), a mixing device configured to receive the milk-based fluid and prepare a milk based product, a nozzle in fluid association with the mixing device for dispensing the milk based product, a product flowpath configured for directing the milk based product to flow from the interface connection through the mixing device to the nozzle, and a clean-in-place flowpath assembly located in the dispenser and comprising a supply of cleaning or sanitizing fluid and a flowpath which is configured to deliver the cleaning or sanitizing fluid to or through the product flowpath. The invention also relates to a method of using and machine readable program for controlling the automated food product dispenser of the invention.

20 Claims, 19 Drawing Sheets

U.S. PATENT DOCUMENTS

| | | | |
|---|---|---|---|
| 6,564,698 B2 | 5/2003 | Rolland | 99/452 |
| 6,685,059 B2 | 2/2004 | Jones et al. | 222/129.1 |
| 2002/0074350 A1 | 6/2002 | Jones et al. | 222/146.5 |
| 2004/0001906 A1 | 1/2004 | Carhuff et al. | 426/130 |

FOREIGN PATENT DOCUMENTS

| | | |
|---|---|---|
| EP | 0 245 641 A1 | 11/1987 |
| EP | 0 579 051 A2 | 1/1994 |
| GB | 2 367 105 A | 3/2002 |

CLEANING CONFIGURATION

CLEAN-IN-PLACE AUTOMATED FOOD OR BEVERAGE DISPENSER

CROSS-REFERENCE TO RELATED APPLICATIONS

This application is a continuation of application Ser. No. 10/328,826 filed Dec. 24, 2002, now U.S. Pat. No. 6,889,603 the entire content of which is expressly incorporated herein by reference thereto.

BACKGROUND

1. Field of the Invention

The present invention relates to food product dispensing equipment and, more particularly, to the cleaning in place of areas of a food dispensing device that uses microbiologically sensitive starting material in the reconstitution and dispensing of food to the consumer. More particularly, but not exclusively, the invention relates to the automatic cleaning of beverage dispensers that use microbiologically sensitive starting components such as milk or milk liquid based concentrate.

2. Background of the Invention

In the foodservice area, post-mix beverage dispensers are well known which mix a concentrate or syrup with several measures of water and then dispense the mixture on demand to reconstitute a hot or cold beverage such as juice, carbonated sodas, coffee or tea. Serious sanitary problems may occur with microbiologically sensitive products such as low acid starting components that can enter into the composition of an on-demand prepared beverage. Other food dispenser may easily be subjected to bacterial contamination and growth such as soft ice cream serving machines.

For instance, milk is naturally a low acid fluid comprising a relatively balanced proportion of proteins, lipids and fluids with a pH of about 6.7. This formulation provides a favorable ground for critical bacterial growth. Milk can rapidly spoil when it comes into contact with contaminated moisture, dust, fluid, etc., and thus proper handling and dispensing of such a product can be challenging.

Therefore, a food dispenser handling liquid milk based components requires regular and thorough cleaning with appropriate cleaning solutions to remove food residues in the tubing and mechanical parts that are in contact with the food product, such that they are sanitized and rinsed properly. If done manually, this process is very laborious, time consuming and expensive in manpower. The cleaning process requires disassembly and re-assembly of the main functional parts of the machines. For instance, employee labor required to properly clean a cappuccino delivering machine or a visual bowl dispenser requires an average of 30 minutes a day. Furthermore, neglect or error in the cleaning process may not only affect the quality of the beverage but also lead to serious hygienic hazards.

Therefore, there is a need for conveniently, reliably and automatically cleaning the areas of a food dispenser that come into contact with a milk based component on a regular basis.

U.S. Pat. No. 6,287,515 to Koosman et al. relates to a cleaning and sanitizing assembly for clean in place food and beverage automatic dispensing machines. The assembly includes at least one water line and at least one sanitizer line to introduce at least one sanitizer to condition water from the at least one water line. The at least one sanitizer may be ozone generated by an ozone generator from air filtered and dried in an air filter/dryer and then added to the water in an air flow apparatus. Typically, the sanitized water is introduced into the dispensing machine through a tank which normally contains the food product mix. The sanitized water is dispersed into the tank through a rinse tube or a spray nozzle extending across the top of each reservoir. Both the rinse tube and spray nozzle may be moved away from the tank should access to the tank become necessary. A cover over the rinse tube and spray nozzle prevents splashing of the sanitized water. From the tank, the sanitized water proceeds throughout the dispensing machine to self-clean food and beverage contact surfaces. However, using an ozone generator with this system has a number of disadvantages. Ozone generators tend to be expensive and bulky. The U.S. Environmental Protection Agency has placed also strict limits on ozone concentrations in the air. Ozone can damage the lungs when inhaled. Thus, ozone devices used for purifying water need to provide protection against the ozone being released from the water and creating high local ozone concentrations in the air surrounding the dispenser. Ozone generators also require high voltage generation since they normally rely on using a corona discharge to create ozone from oxygen. As a result, safety considerations arise due to the use of high voltage, and relatively high electrical power consumption occurs. Sometimes a purified oxygen source is also required. Moreover, since ozone is very reactive, it cannot be stored in water, and must be generated on demand by the system.

U.S. Pat. No. 6,240,952 to Schroeder relates to an aseptic product dispensing system that includes a sanitary connection assembly interposed in fluid communication with a substantially conventional aseptic product source and a substantially conventional product dispenser. The sanitary connection is provided with an automated cleaning system whereby a combination of pressurized gas, flushing fluid and/or sanitizing solution may be injected into, and thereafter evacuated from, the sanitary connection assembly. A controller is connected to each source for selectively delivering the selected fluid to sanitary connection and through out the dispenser. The selected fluid is then evacuated through the terminal valve of the dispenser. The cleaning protocol is such that water is circulated first, then a sanitized fluid is circulated and maintained for a certain time in a soak cycle. Finally, a pressurized gas is circulated to displace water and/or sanitized solution remaining in the system up to the dispensing valve. This clean-in-place system is cumbersome and complicated due to the number of sanitizing/rinsing lines and the same number of sanitizing/rinsing sources corresponding to those lines. Therefore, this system is more adapted for being installed outside and in connection with a traditional dispenser. Furthermore, the system is very much sanitizer consuming in the sense that the sanitizer flows through the dispenser and is evacuated through the dispensing valve. For reducing the volume of sanitizer flowing through the dispenser, the cleaning protocols provides a soaking cycle in which the sanitizer remains for a certain time within the system. However, in order to be effective, soaking must be maintained during several hours which means that a full cleaning protocol can only be carried out overnight.

Therefore, there is a need for a clean-in-place system that is more simple, less cumbersome, less product and time consuming and less expensive than in the known existing systems. The present invention now satisfies these needs.

SUMMARY OF THE INVENTION

The invention relates to an automated food product dispenser comprising an interface connection configured to establish a supply of a milk-based fluid from a reservoir (for example, a container or a bag), a mixing device configured to receive the milk-based fluid and prepare a milk based product, a nozzle in fluid association with the mixing device for dispensing the milk based product, a product flowpath configured for directing the milk based product to flow from the interface connection through the mixing device to the nozzle, and a clean-in-place flowpath assembly. The assembly is located in the dispenser and includes a supply of cleaning or sanitizing fluid and a flowpath which is configured to deliver the cleaning or sanitizing fluid to or through the product flowpath.

The invention also relates to a method for automatically cleaning, in a food or beverage dispenser, a product flowpath configured for establishing connection with at least one milk based fluid. This method includes the steps of providing a rinsing, cleaning or sanitizing fluid within the dispenser, circulating the fluid at a particular velocity to or through the product flowpath of the dispenser to clean it, and recirculating the fluid. Advantageously, however, the rinsing, cleaning or sanitizing fluid is recirculated in a loop from the product flowpath back to a buffer reservoir that receives a buffer volume of the fluid. Periodically, the recycled rinsing, cleaning or sanitizing fluid can be drained from the dispenser and discarded.

The invention also relates to a clean-in-place system for an automated dispenser comprising a product flowpath configured to supply a milk based fluid. This system includes at least one source of rinsing, cleaning or sanitizing fluid, a buffer reservoir configured to initially retain the rinsing, cleaning or sanitizing fluid, a clean-in-place flowpath assembly configured in a loop to recirculate at a certain velocity the rinsing, cleaning or sanitizing fluid from the buffer reservoir in or through all or part of the product flowpath and then back to the buffer reservoir, a drain for draining the rinsing, cleaning or sanitizing fluid, and a controller and a timer to time control the circulation of the rinsing, cleaning or sanitizing fluid through the clean-in-place flowpath assembly and to recirculate it to the buffer reservoir or to evacuate it to the drain.

In another aspect of the invention, a machine readable program is provided that contains instructions for controlling a dispenser to dispense a milk-based product, wherein the dispenser has an interface connection, a mixing device, a nozzle in fluid association with the mixing device, a product flowpath and a clean-in-place flowpath assembly located in the dispenser including a supply of cleaning or sanitizing fluid and a flowpath. The machine readable program provides means for preparing a rinsing, cleaning or sanitizing fluid within the dispenser, means for circulating the fluid at a predetermined velocity to or through the product flowpath of the dispenser to clean it, and means for recirculating the fluid through the clean-in-place flowpath.

It is to be understood that both the foregoing general description and the following detailed description are exemplary and are intended to provide further explanation of the invention claimed.

BRIEF DESCRIPTION OF THE DRAWINGS

The accompanying drawings, which are incorporated in and constitute part of this specification, are included to illustrate and provide a further understanding of the system, method and machine readable program of the invention. Together with the description, the drawings serve to explain the principles of the invention, wherein.

DETAILED DESCRIPTION OF THE PREFERRED EMBODIMENT

Figure 1:
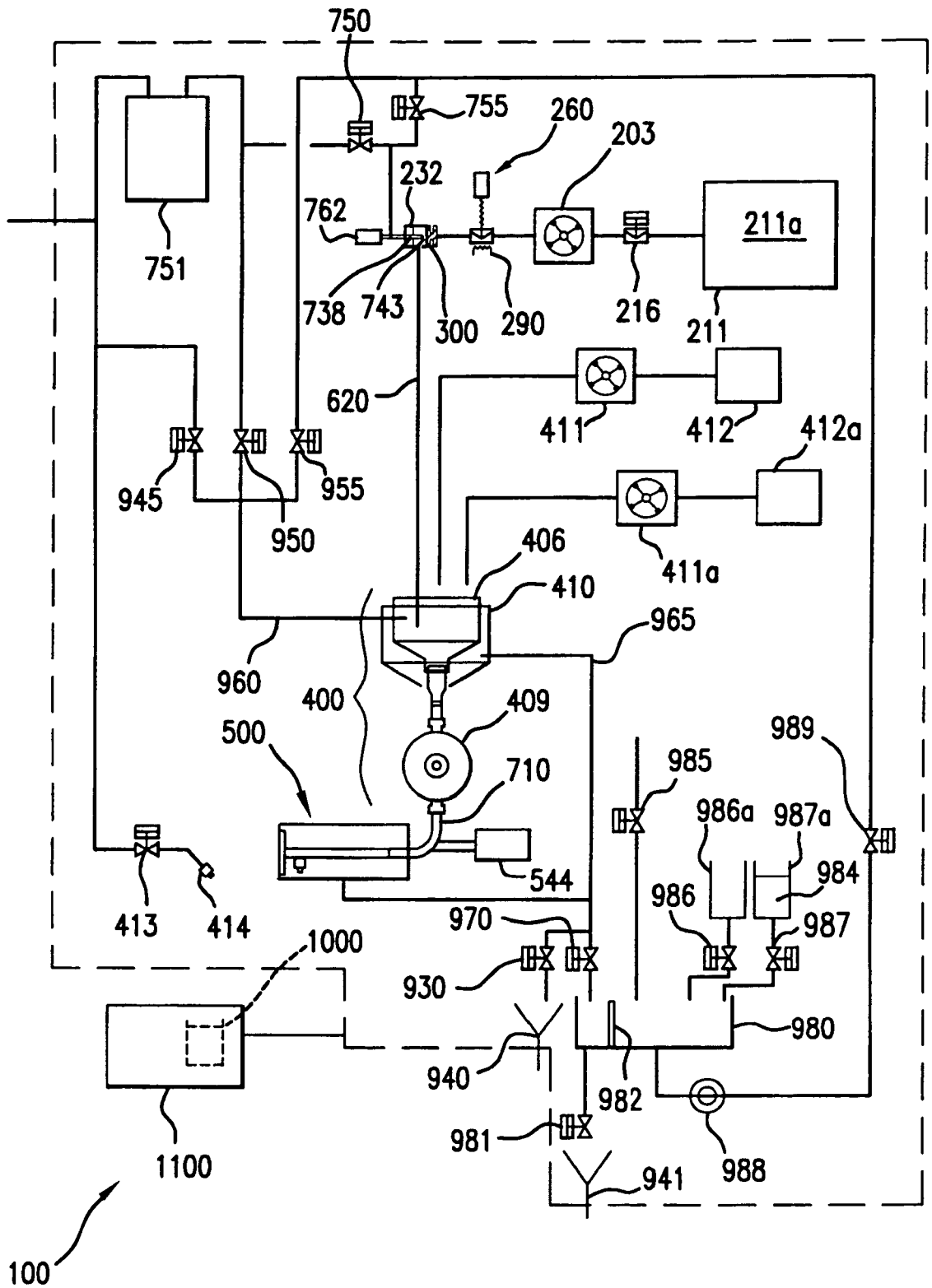
FIG. 1 is a schematic representation of a representative embodiment of the automated food product dispenser in accordance with the invention showing all major components of the dispenser.

Reference will now be made in detail to the present preferred embodiments of the invention, an example of which is illustrated in the accompanying drawings. The device presented herein may be used to dispense liquid-based food products. The present invention is particularly suited for mixing and dispensing milk-based liquid food products, since it contains a programmable self-cleaning mechanism that can help to avoid spoilage of milk-based food product within the food product flowpath.

The supply of cleaning or sanitizing fluid is preferably produced within the dispenser by mixing a chemical cleaning concentrate, supplied from a concentrate supply, with water supplied from a water supply to generate a chemical cleaning agent for use as the cleaning fluid. Also, the clean-in-place flowpath assembly can include a buffer reservoir configured to receive a buffer volume of the cleaning or sanitizing fluid, a loop line associated with the reservoir and configured to provide circulation of the fluid from the reservoir through the product flowpath and back to the reservoir, and a drain associated with the assembly for removing fluid therefrom. Thus, the fluid cleans the product flowpath as it flows thereon or therethrough. The dispenser preferably includes a water supply and heater, wherein the cleaning or sanitizing fluid can be produced by heating water from the water supply in the heater at a temperature effective to provide a sanitizing effect.

A central controller can be used for controlling a full cleaning-in-place process. The controller will generally include a timer or other periodic energizing device. The dispenser can also include a control panel, wherein the central controller can be programmed to run the full cleaning-in-place process in response to user demand. Alternatively or additionally, the central controller can be programmed to automatically run a time controlled delivery of one cleaning cycle of the chemical cleaning agent through the product flowpath, followed by a time controlled delivery of at least one sanitizing cycle of heated fluid through the product flowpath. Advantageously, the controller is programmed to provide a pre-rinsing cycle in the full cleaning-in-place process that takes place just before the cleaning cycle.

The dispenser preferably includes a removable container that contains a source of a cleaning concentrate and is connected in the clean-in-place flowpath assembly to a shut-off valve that is controlled by the controller to deliver and to optionally meter an amount of cleaning concentrate to the buffer reservoir for preparing the cleaning agent for sanitizing of the product flowpath.

In a preferred embodiment, the interface connection is adapted to engage a milk based fluid reservoir that includes having a reservoir, a portion of hose and a fitment. In this arrangement, the connection comprises a fluid chamber comprising a cleaning fluid inlet that allows for the cleaning fluid to enter the chamber, a product inlet for the milk based fluid to enter the chamber and a product outlet for the product to exit the chamber to the product flowpath. Also included is connection means at the product inlet configured for hygienically and removably connecting the fitment to the milk based fluid reservoir and the fluid chamber. Such means preferably includes a spring-loaded releasable collar, protrusions or arms that can hold the fitment in place when the dispenser is operating, or may include any other devices such as threaded or snap fittings as are well-known in the art. In addition, the connection includes a flexible hose for directing the milk based fluid from the reservoir the mixing device, a valve adapted and controlled by the controller to operatively engage the flexible hose portion to selectively block the flow of the milk based fluid at a closing point, and projection means for promoting cleaning of the fitment and flexible hose portion up to the closing point. The projection means preferably includes a manually or automatically movable shaft with a pointed or narrowed end to protrude into the fitment and assist in directing cleaning fluid into the same, and could also include other devices such as pressurized liquid jets with or without moveable or spring loaded brushes or cleaning devices to project cleaning or sanitizing fluid into the fitment.

The mixing device of the dispenser preferably includes a mixing bowl to collect the milk based fluid, water and other beverage forming components, and a whipper to mix the milk based fluid, water and other beverage forming components together to form the milk based product. Thus, the clean-in-place flowpath assembly will include a mixing bowl feed line for directly directing cleaning or sanitizing fluid to the mixing bowl for cleaning the mixing bowl and the product flowpath that is arranged downstream of the mixing bowl. To do this, the clean-in-place flowpath assembly comprises one or more valves controlled by the controller to selectively open or close either the feed line or a portion of the product flowpath. Also, the mixing bowl can include an outer skirt that surrounds the mixing bowl and includes a fluid outlet connected to a downstream cleaning fluid evacuation conduit of the clean-in-place flowpath assembly. By configuring the outer skirt to collect fluid that overflows the mixing bowl, the downstream cleaning fluid evacuation conduit can selectively direct the collected fluid to the buffer reservoir to recirculate the cleaning fluid, or to the drain. The whipper can be controlled to run intermittently to assist in making the cleaning fluid overflow the bowl when the whipper is in a turn-off mode and, to assist in driving the cleaning fluid through the bowl and product flowpath to the nozzle when the whipper is in a turn-on mode. When running, the whipper may be configured to direct flow to the nozzle. When off, the fluid overflows the mixing bowl.

The dispenser nozzle can be controlled by the controller to be positioned in either a dispensing position wherein the prepared beverage is dispensed to a dispensing zone, or a cleaning position wherein the nozzle is in fluid communication the buffer reservoir to recirculate cleaning fluid or drain cleaning fluid from the mixing bowl.

These features enable the dispenser to operate at room temperature such that a refrigeration or freezing unit associated with the milk based fluid reservoir is not necessary.

When the food or beverage dispenser includes a product mixing bowl, the method can preferably includes directly directing the rinsing, cleaning or sanitizing fluid to the mixing bowl for cleaning the mixing bowl and the product flowpath that is arranged downstream of the mixing bowl. The mixing bowl can be cleaned by filling the bowl to overflow with the rinsing, cleaning or sanitizing fluid, collecting fluid that overflows the bowl, and selectively directing the collected fluid back to the buffer reservoir to recirculate the cleaning fluid or to a drain to remove the collected fluid from the dispenser.

As noted above, the circulation of the rinsing, cleaning or sanitizing fluid can be automatically conducted at periodic intervals of non-use of the dispenser or upon demand by a user. If desired, the product flowpath can be pre-rinsed prior to circulation of the rinsing, cleaning or sanitizing fluid. Also, a portion of the product flowpath can be closed off so that remaining portions of the product flowpath can receive the rinsing, cleaning or sanitizing fluid.

In accordance with a further aspect of the invention, a machine readable program is provided that further includes means for recirculating the rinsing, cleaning or sanitizing fluid in a loop from the product flowpath back to a buffer reservoir that receives a buffer volume of the fluid. Such means for recirculating may include, for example, a pump controlled by a controller or a valve manifold capable of driving a flow through the fluid loop by introducing liquid at a higher pressure through the fluid loop. Optionally, means for periodically draining and discarding the recycled rinsing, cleaning or sanitizing fluid from the dispenser may also be provided. Such means for periodically draining may include, for example, a solenoid operated valve located in a drain line that may be selectively opened by a controller to permit gravity or pressure driven draining of the reservoir. Additionally or alternatively, means may also be provided for directly directing the rinsing, cleaning or sanitizing fluid to a mixing bowl within the dispenser for cleaning the mixing bowl and the product flowpath that is arranged downstream of the mixing bowl. Such means for directly directing the fluid may include, for example, a valve manifold containing solenoid operated valves that can be selectively opened or closed by a controller wherein the manifold may be selectively configured to direct hot water or water based solution containing a cleaning concentrate to the mixing bowl and portions of the product flowpath downstream from the mixing bowl.

In further accordance with the invention, a machine readable program may be provided that further includes means for cleaning the mixing bowl by filling the bowl to overflow with the rinsing, cleaning or sanitizing fluid; means for collecting fluid that overflows the bowl; and means for selectively directing the collected fluid back to the buffer reservoir to recirculate the cleaning fluid or to a drain to remove the collected fluid from the dispenser. The means for cleaning the mixing bowl may include a solenoid actuated valve manifold controlled by a controller that is configured to fill the mixing bowl to an overflowing condition. The means for collecting fluid that overflows the bowl may include, for example, a skirt surrounding the mixing bowl that is connected to a drain line. The means for selectively directing the collected fluid back to the buffer reservoir may include a solenoid actuated valve manifold controlled by a controller that is configured to selectively open and close valves and/or turn on pumps to direct the collected fluid back to the buffer reservoir and/or to a drain to remove the collected fluid from the dispenser.

Additionally or alternatively, the machine readable program may still further include means for automatically conducting circulation of the rinsing, cleaning or sanitizing fluid at periodic intervals of non-use of the dispenser or upon demand by a user. Such means for automatically conducting circulation of the fluid may include, a solenoid actuated valve manifold controlled by a controller that is configured to selectively open and close valves and/or turn on pumps to automatically circulate the rinsing, cleaning or sanitizing fluid at periodic intervals of non-use of the dispenser or upon demand by the user.

Optionally, means may also be provided for pre-rinsing the product flowpath prior to circulation of the rinsing, cleaning or sanitizing fluid. Also, means for closing off a portion of the product flowpath so that remaining portions of the product flowpath can receive the rinsing, cleaning or sanitizing fluid may be present. Each of these means preferably includes, a solenoid actuated valve manifold controlled by a controller that is configured to selectively open and close valves and/or turn on pumps to pre-rinse the product flowpath prior to circulation of the rinsing, cleaning or sanitizing fluid and to close off a portion of the product flowpath so that remaining portions of the product flowpath can receive the rinsing, cleaning or sanitizing fluid, respectively.

For purposes of explanation and illustration, and not limitation, an exemplary embodiment of the device in accordance with the invention is shown in FIG. 1 and is designated generally by reference character 100.

In accordance with the present invention, the automated food product dispenser comprises an interface connection that is configured to establish a supply of a milk based fluid from a milk based fluid reservoir, a mixing device configured to receive the milk based fluid and prepare a milk based product, a nozzle in fluid association with the mixing device to dispense the milk based product, a product flowpath configured to direct the milk based product to flow from the interface connection through the mixing device to the nozzle, and a clean-in-place flowpath assembly located in the dispenser and including a supply of cleaning or sanitizing fluid and a flowpath which is configured to deliver the cleaning or sanitizing fluid to or through the product flowpath.

Dispenser 100 includes interface connection 233 that is configured to establish a supply of a milk based fluid 211$a$ from a milk based fluid reservoir 211, a mixing device 400 configured to receive the milk based fluid 211$a$ and prepare a milk based product, a nozzle 500 in fluid association with the mixing device 400 to dispense the milk based product, a product flowpath 600 configured to direct the milk based product to flow from the interface connection 233 through the mixing device 400 to the nozzle 500, and a clean-in-place flowpath assembly 700 located in the dispenser 100 and including a supply 987$a$ of cleaning or sanitizing fluid and a flowpath 800 which is configured to deliver the cleaning or sanitizing fluid to or through the product flowpath 600.

Each of the above referenced features will be described below in further detail, after which the device as a whole will be discussed, including some exemplary modes of product preparation and delivery as well as self-cleaning operations of the device.

Figure 2:
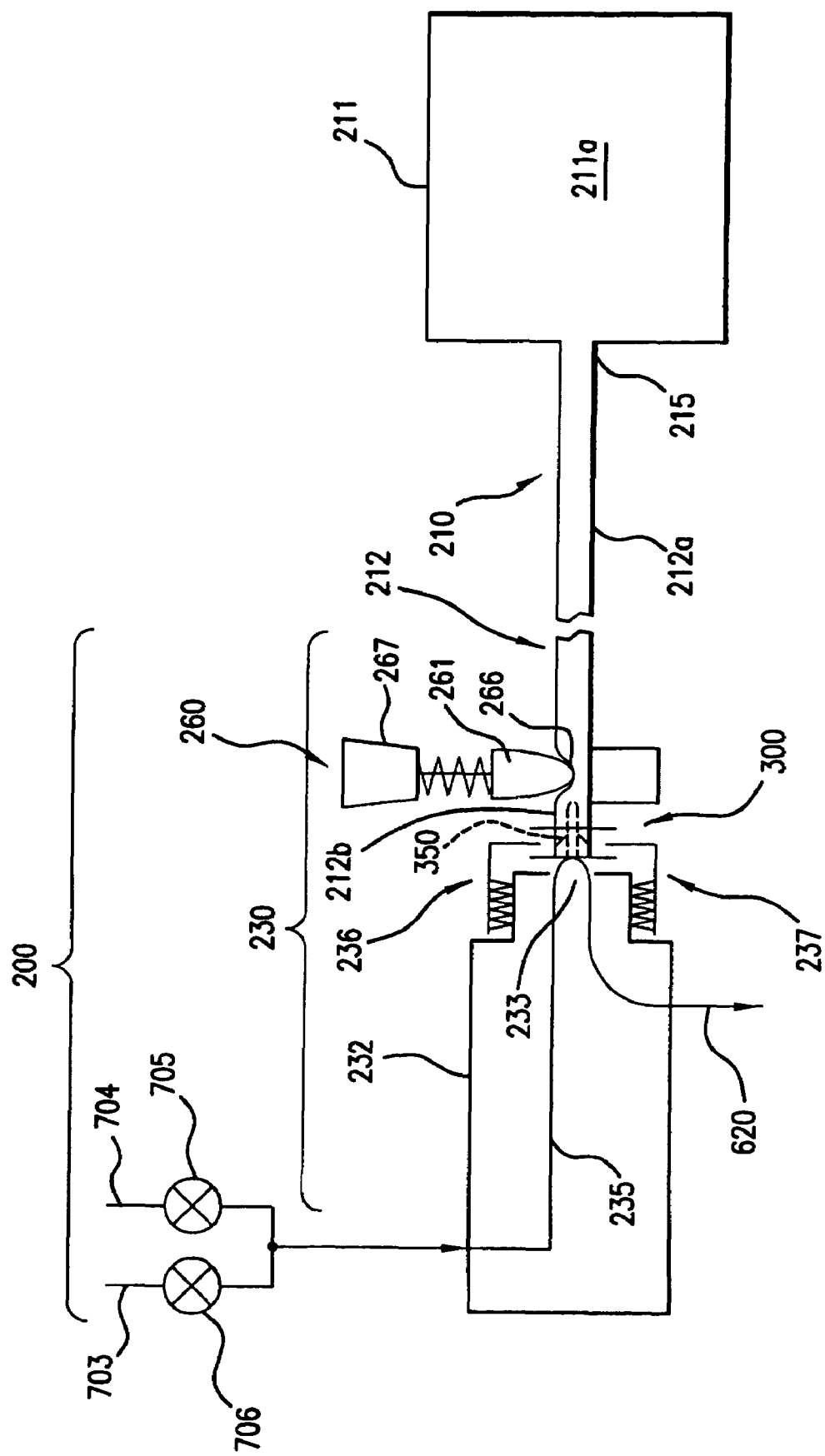
FIG. 2 is a partial schematic representation of the automated food product dispenser of FIG. 1 showing the milk manifold.

FIG. 2 depicts the interface connection 233 and structures associated therewith. The interface connection 233 is configured to establish a supply of a milk based fluid 211$a$ from a milk based fluid reservoir 211 to a dispensing line 620. The milk manifold 230 includes a disposable sub-assembly or container assembly 210 that is removably attached to a milk manifold 230. The milk manifold 230 comprises a housing 232 having an interface connection 233 for establishing beverage or food fluid connection from the container assembly 210 to a dispensing line 620. The manifold system is adapted for being traversed and flushed through a flushing line 235 by cleaning or sanitizing fluids. The cleaning or sanitizing fluids may encompass hot water 820 or cold water 810, chemical agents, steam, and combinations thereof. The cleaning or sanitizing fluids can be selectively sent through flushing line 235, for example, by selectively opening and closing valves that may place flushing line 235 in fluid communication with a source of cleaning or sanitizing fluid (See FIG. 1) wherein the valves are controlled by a programmable controller 1000.

The container assembly 210 preferably includes a package or reservoir 211 containing the beverage or food base, a hose 212 that terminates by a fitment 300. The package or reservoir 211 may typically be a bag-in-box type package or any similar disposable flexible package that is easy and convenient for transportation and storage. The hose 212 may preferably be directly sealed or crimped to the package port 215 and be made of materials that are compatible for sealing with the package material. The container assembly 210 with its membrane 350 may preferably be sterilized, such as by irradiation, prior to filling. Filling of the food liquid is preferably aseptically done. Aseptic filling may be carried out by a filling port or aperture provided in the package itself or by filling the fitment 300 attached to the hose which is subsequently properly sealed. Therefore, such a container assembly 210 can be maintained aseptic until the membrane 350 is punctured or, alternatively peeled off which provides the benefit to transport, store and load the container assembly 210 in the dispensing unit at ambient temperature without need for refrigeration. Such a flexible reservoir and hose assembly is described in further details in U.S. Pat. No. 6,024,252 to Clyde entitled: "Dispenser System"; the content of which is expressly incorporated herein by reference.

The container assembly 210 is connected to the manifold system 230 with its fitment 300 connected to the interface connection 233 and the hose 212 engaged in a pinch valve 260 or similar structure that can maintain the upstream portion 212a of the hose 212 and package or reservoir 211 sterile. Additional valves such as valve 216 and a pump 203 are usually provided to ensure a control of the flow of product to the dispensing line 620 (See FIG. 1).

The milk manifold 230 comprises retaining means 236 that complementarily engages in a convenient and removable manner to the terminal fitment 300 of the invention. The configuration of the coupling means 236 may widely vary depending upon the type and shape of the fitment to be locked at the interface connection 233. The coupling should be able to provide a watertight connection at the interface connection 233 in order to establish a reliable and secure fluid communication between the container assembly 210 and the dispensing line 620 of the milk manifold 230. Preferably, there is provided a spring loaded holding system 237 adapted to engage the coupling means 236 of the fitment 300 that elastically forces the fitment 300 to the interface connection 233. It is clear that the connection between the fitment 300 and the manifold system 230 could be carried out by any other equivalent means such as by cam or lever type mechanisms to provide substantially the same result without departing from the spirit of the invention.

In a cleaning or rinsing mode, the manifold system 230 is capable of directing cleaning or sanitizing fluid within the fitment 300 up to the pinch point 266 so as to regularly clean or rinse this portion of the container assembly. In such a configuration, the pinch valve 260 ensures the upstream part of the container assembly 210 remains isolated and sterile. Importantly, it can be easily understood that the shortened construction of the fitment 300 enables to effectively reduce the downstream portion 212b of the hose 212 that requires cleaning or rinsing. The fitment 300 also gives very little opportunity for micro-organisms to settle as contact with the fluid is confined along a short tubular internal surface. Hence, the hygienic conditions of dispensed milk based fluids can be successfully improved and the risks of bacterial contamination and growth are proportionally reduced. As a result, an aseptically processed container containing low acid concentrate such as milk concentrate with relatively low water activity can be dispensed at ambient temperature in the dispensing unit without requiring refrigeration of the container.

In accordance with the invention, an automated food product dispenser is provided that further comprises a mixing device configured to receive the milk based fluid and prepare a milk based product.

Figure 3:
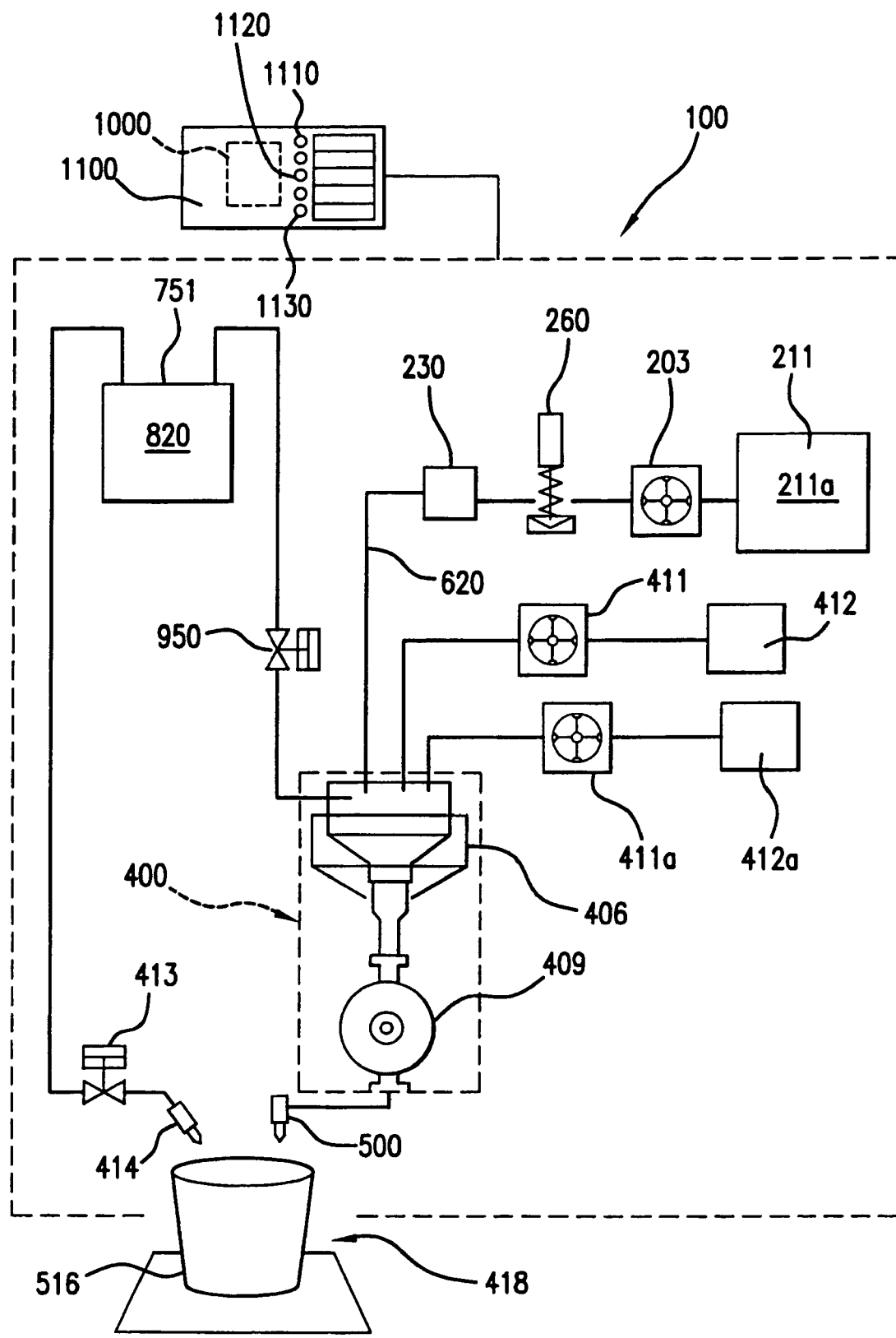
FIG. 3 is a partial schematic representation of the automated food product dispenser of FIG. 1 also showing a control panel and controller.

FIGS. 1 and 3 illustrate a mixing device 400 in accordance with the invention. In using this embodiment of the invention, an operator selects the desired beverage, for example a cappuccino, from the command panel 1100 of the device. Preferably an electronic controller 1000 actuates the preparation process of the milk-based beverage and operates the different parts of the dispenser 100 apparatus described herein. A flow of milk based fluid 211, preferably a milk concentrate, from reservoir 211 can be supplied via the milk manifold 230 as described above. A pump 203, preferably a peristaltic pump, can provide pressure to force milk based fluid 211a past pinch valve 260 to a mixing bowl 406, which is connected to a whipper 409.

The mixing bowl 406 and whipper 409 are part of a mixing device 400. While milk based fluid 211a flows to the mixing bowl 406, hot water supply valve 950 is opened to begin a flow of hot water 820 from a hot water 820 tank 751 to the mixing bowl 406 where hot water 820 and milk based fluid 211a begin to mix together. Mixing bowl 406 is activated for mixing the blend of hot water 820 and milk based fluid 211a. Then the hot reconstituted milk mixture 211b flows from the bowl 406, through the whipper 409, through the dispensing nozzle 500 and into a receptacle, such as a cup 516, which is received in a dispensing area 418. This step occurs for a predetermined period to achieve dosage of hot water 820 and milk based fluid 211a for preparing an individual serving of the beverage. After this period, milk pump 203 is turned off. The dispensing area 418 is preferably dimensioned for receiving a drinking cup or glass, and for positioning the nozzle at less than about 10 cm above the beverage surface, although other distances may be employed in other embodiments.

After a predetermined delay, preferably of about one second, whipper 409 is shut off, and a coffee pump 411 is turned on for delivering coffee concentrate, preferably in controlled doses, from a coffee container 412 to the mixing bowl 406. Alternatively, in the case the beverage product prepared is a hot chocolate beverage, pump 411a is turned on for sampling chocolate concentrate from a chocolate container 412a. Containers 412 and 412a are preferably of the same or similar kind of construction as the reservoir 211, e.g., hermetically sealed removable pouches, but may also be very different from each other in other embodiments. Coffee and hot water 820 flow into the mixing bowl 406, through the whipper 409, and through the nozzle 500 and into the cup 516, for a predetermined time and at a selected rate to achieve desired dosage of coffee and hot water. After the coffee dosage has been achieved, coffee pump 411 is turned off.

Figure 4:
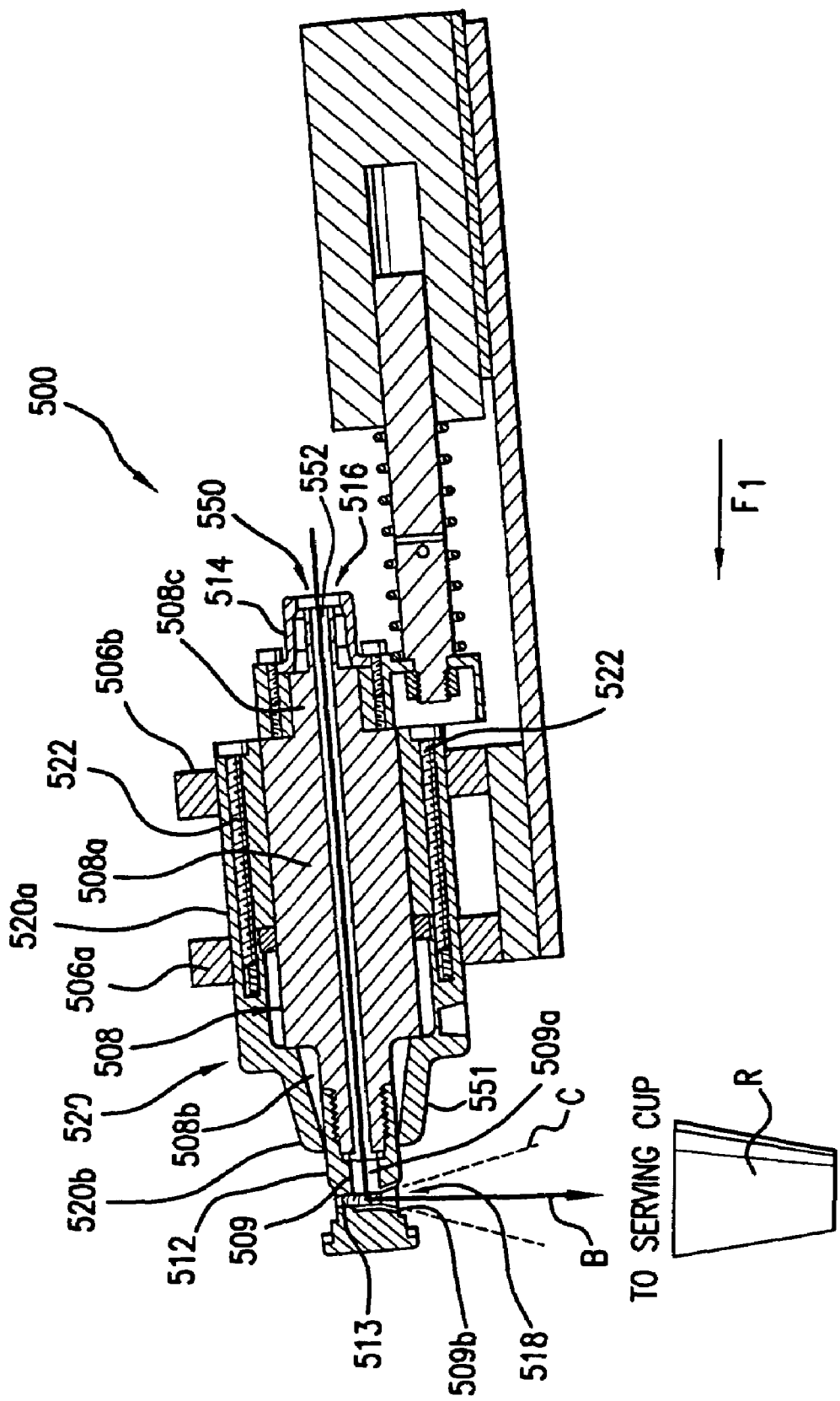
FIG. 4 is a partial schematic representation of the automated food product dispenser of FIG. 1 showing the dispensing nozzle in a dispensing position.

In further accordance with the invention an automated food product dispenser is provided that utilizes a nozzle in fluid association with the mixing device to dispense the milk based product. As shown in FIG. 3, a dispensing nozzle 500 is provided. Preferably, the nozzle 500 is capable of self-cleaning. Referring to FIG. 4, nozzle 500 comprises a body 508 of generally cylindrical shape. Body 508 comprises a middle section 508a, and two end sections 508b, and 508c, each having a smaller diameter than that of middle section 508a. Body 508 is provided with a through conduit 550 extending longitudinally at the center of body 508. Conduit 550 comprises a first end portion 551 to which a nozzle head 512 is connected and a second end portion 552 intended to be connected to a fluid feed line (not shown) via a conduit (also not shown). In this example, nozzle head 512 is screwed onto the free end of section 508b of body 508 and a connector 514 is secured to the free end of section 508c. Nozzle head 512 comprises a channel 509 bent at a right angle having a first portion 509a connected to conduit 510 and a second portion 509b opening out onto the exterior and in which a beveled cylinder 513 is screwed. Beveled cylinder 513 delimits with portion 509b of channel 509 an annular fluid or beverage orifice 518, the shape of which determines the shape of the fluid jet. In the example illustrated in FIG. 4, the jet has the shape of a cone C shown in dotted lines. Connector 514 thus defines a fluid or beverage inlet 516 and the fluid or beverage orifice 518 defines a fluid or beverage outlet.

It will be noted that screwing nozzle head 512 onto body 508 and screwing beveled cylinder 513 into nozzle head 512 enables these elements to be easily interchanged and makes dispensing nozzle 500 advantageously flexible. In particular, dispensing nozzle 500 can be rapidly and easily adapted to beverages requiring different sizes for beverage outlet 518 or different jet shapes. Dispensing nozzle 500 further comprises a collector member 520 that has the general shape of a cylindrical sleeve open at both ends. Collecting sleeve 520 has a cylindrical rear section 520a extended by a converging truncated front section 520b. Sleeve 520 is secured in brackets 506a, 506b. In the example shown, sleeve 520 is made of two parts connected to each other by a plurality of screws 522 extending longitudinally in the thickness of the walls of said sleeve parts. Body 508 and nozzle head 512 are guided and slide axially inside sleeve 520.

Figure 5:
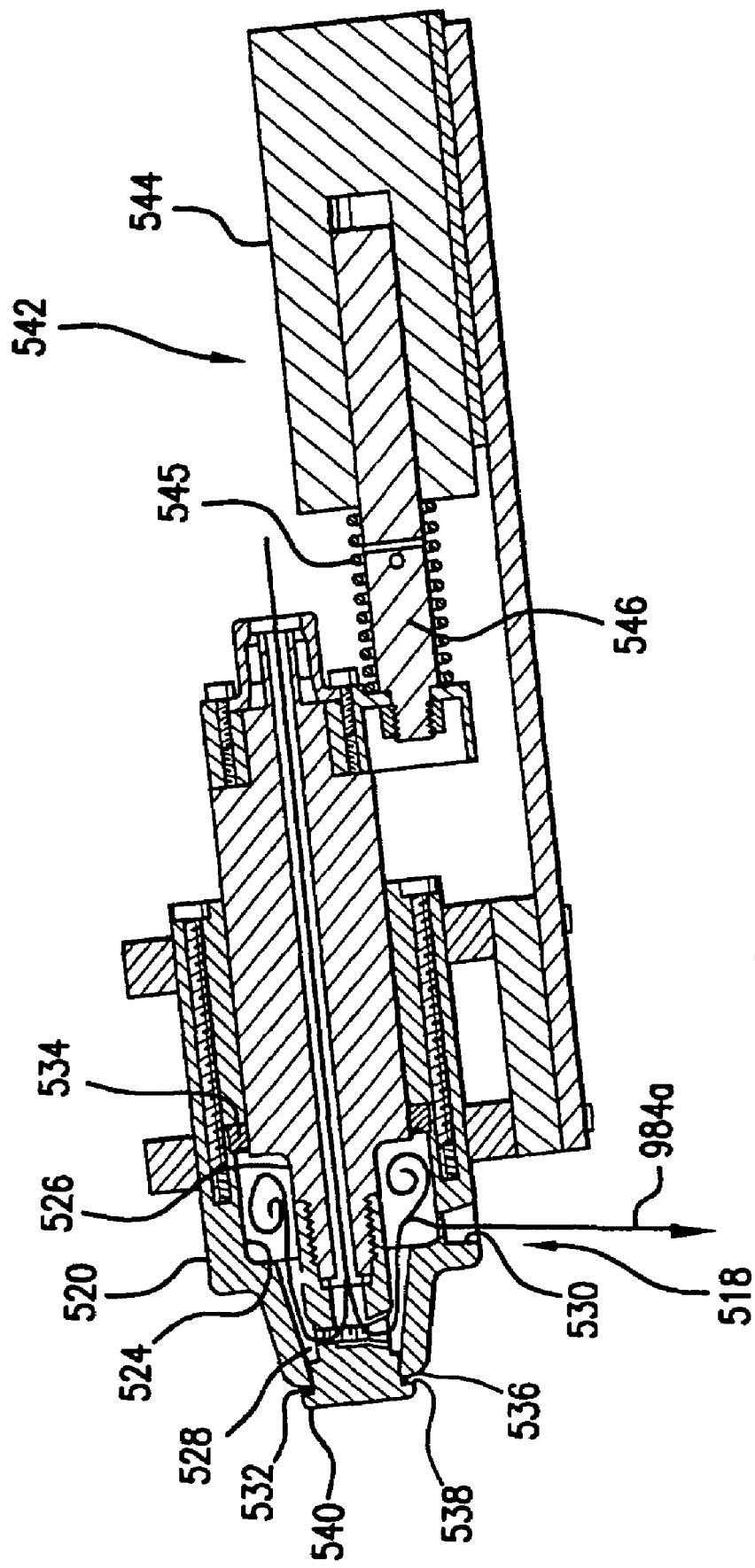
FIG. 5 is a partial schematic representation of the automated food product dispenser of FIG. 1 showing the dispensing nozzle in a cleaning and/or sanitizing position.

More precisely, body 508 and nozzle head 512 are mobile relative to sleeve 520 between a first position, called the dispensing position, shown in FIG. 4, in which nozzle head 512 is released from sleeve 520, i.e. it is outside sleeve 520 so as to be able to dispense a beverage into a receptacle R, and a second position called the cleaning position shown in FIG. 5, in which at least a part of sleeve 520 is placed in front of beverage outlet 518 to collect a cleaning fluid 984a coming out of the beverage outlet 518.

In the dispensing position, nozzle head 512 projects from the front section 520b of sleeve 520 and a beverage B arriving via conduit 550, symbolized by a bold line in FIG. 4, can be dispensed through beverage outlet 518 of nozzle head 512 into a receptacle R arranged below beverage outlet 518.

In the cleaning position, inner wall 524 of sleeve 520 defines with the outer surface 526 of body 508, a cleaning chamber 528 in which the nozzle head 512 and in particular beverage outlet 518 is housed. Cleaning chamber 528 communicates with the exterior via a drain orifice 530 located in an inner wall of sleeve 520. Depending on the particular case, drain orifice 530 is connected either to the sewage system (not shown), or to a recuperation tank (such as CIP tank 980, See FIG. 1) in order to allow the cleaning fluid to be put back into circulation in a closed circuit via a tank and a pump device (not shown). Two sealing gaskets, front gasket 532 and back gasket 534, are arranged on either side of beverage outlet 518, and act to seal chamber 528.

Preferably, front gasket 532 is formed by a sealing joint and is arranged between a front surface 536 of truncated section 520b around the front opening of sleeve 520 and a complementary surface 538 defined by a collar 540 provided in the front part of nozzle head 512.

It will be noted that collar 540 is located outside sleeve 520 whether dispensing nozzle 500 is in the dispensing position or in the cleaning position. It will be noted that frontal surface 536 and complementary surface 538 are preferably planar in order to assure proper sealing of chamber 528 in the cleaning position. Back gasket 534 is formed by a sealing joint arranged between the cylindrical portion of inner wall 524 of sleeve 520 and median section 508a of body 508. Typically, front sealing gasket 532 is an O-ring type joint and back sealing gasket 534 is a lip seal type joint. In the cleaning position, body 508 is moved so that collar 540 abuts against frontal surface 536 in order to make chamber 528 watertight.

Thus, a cleaning fluid or caustic solution, 984a symbolized by a bold line in FIG. 5, passing through conduit 550, can flow into conduit 509 of nozzle head 512, then into chamber 528, and around nozzle head 512 before flowing through outlet 530 into the sewage system or a recuperation tank.

In order to assure relative movement between sleeve 520 and body 508, body 508 is connected to actuating means 542 secured to base plate 504. Preferably, actuating means 542 are formed of a solenoid electromagnetic actuator 544 associated with a return spring 545. The rod 546 of actuator 544 is secured to section 508a of body 508 and return spring 545 is arranged around rod 546 between body 508 and actuator 544.

Thus, in response to a control signal originating from a controller 1000 (See e.g., FIG. 3), actuating means 542 allows dispensing nozzle 500 to be automatically brought into its dispensing and cleaning positions. More precisely, in the absence of any signal on actuator 544, the solenoid is de-energized and return spring 545 urges body 508 in the direction of arrow F1 to bring dispensing device 100 into the dispensing position shown in FIG. 4. In the presence of a signal on actuator 544, the solenoid electromagnetic actuator 544 is energized and tends to urge body 508 in the direction of arrow F2 to bring dispensing device 100 into the cleaning position shown in FIG. 5. It goes without saying that any other type of actuator can be used provided it allows a translation movement to be impressed on body 508 with respect to sleeve 520. By way of example, one could envisage replacing electromagnetic actuator 544 with a drive device with gears or by an electric actuator.

Further details regarding the self-cleaning nozzle are described in co-pending U.S. patent application Ser. No. 10/133,126 by Peter W. Carhuff et al. filed Oct. 11, 2002 entitled "FLUID DISPENSING DEVICE WITH SELF-CLEANING NOZZLE AND METHODS OF USE" which, is incorporated herein by reference in its entirety.

In accordance with another aspect of the invention, and referring to FIGS. 1 and 3, after a small delay to deliver the remainder of hot water 820 required by the recipe, the hot water supply valve 950 is turned off. The remainder of the hot water 820 after the milk based fluid 211a and coffee have been added has the advantage to allow for recovery of most of the milk based fluid 211a and coffee remaining in the whipper bowl 406 and whipper 409 from the system and into the cup 516.

Then, a showering valve 413 is turned on for preferably several seconds, as described below, to supply water 810 to a spraying nozzle 414 to spray water 810 on the foam on the top of the cappuccino beverage prepared in the cup 516. This spraying phase acts for washing the brown coffee material from the top layer of the foam to whiten the upper layer of the cappuccino froth topping. It also breaks larger bubbles and moistens the foam to refine the froth structure and to give the froth topping a whipped and creamy appearance and to increase the creaminess and homogeneity of its appearance.

To complete an appropriate spraying of the foam layer and achieve a satisfying whitening and appearance of the foam, care should be given to the water droplet size. A suitable droplet size is obtained by a combination of the nozzle orifice size, the nozzle orifice design and the pressure of the water 810 supplied to the spraying nozzle. The nozzle 414 has preferably an orifice size of about 0.1 to 1 mm, more preferably of from 0.50 to 0.85 mm, and most preferably between 0.7 mm and 0.8 mm. Optimum results were obtained with a nozzle having an orifice size of 0.762 mm.

The nozzle 414 preferably operates to distribute droplets in a diverging configuration on the surface of the froth. A diverging configuration has proved to provide smaller droplets as compared to a straight configuration and form a widespread and uniform washing effect on the froth without creating recessed areas on the surface, although a straight or other configurations can alternately be used. The nozzle 414 preferably has a tapered orifice adapted to form a divergent spray angle ranging of from about 45 to 60 degrees, more preferably about 50 to 55 degrees.

Further details regarding materials and methods for treating the foam using a water spray are described in co-pending U.S. patent application Ser. No. 10/268,777 by Peter W. Carhuff et al. filed Oct. 11, 2002 entitled "FROTH SHOWERING" which, is incorporated herein by reference in its entirety.

In further accordance with the invention an automated food product dispenser is provided that further comprises a product flowpath configured to direct the milk based product to flow from the interface connection through the mixing device to the nozzle.

As embodied herein and with specific reference to FIGS. 1 and 2, the dispensing device 100 of the invention is shown to generally include the milk manifold 230 inserted in fluid communication with the reservoir 211 and a downward dispensing line 620 that can lead to a mixing device 400 as described above, to a delivery conduit 710 and the nozzle 500.

As embodied herein, the product flowpath 500 is any path that food products traverse. For example, during ordinary operation of the dispenser 100, the product flowpath would include any surfaces that come into contact with a food product. This could, of course, include at least the reservoir 211, hose 212, fitment 300, interface connection 233, dispensing line 620, mixing device 400, delivery conduit 710 and nozzle 500 It could also include pumps 411 and 411*a*, coffee container 412, and chocolate container 412*a*. The chocolate and coffee are preferably stored in liquid concentrate form in bag-in-box, or "BIB" type packages. The number of concentrate containers, pumps, dispensing lines etc. that make up the product flowpath are not limited and depend only upon the desired complexity and type of the dispensing device 100.

In further accordance with the invention an automated food product dispenser is provided that further comprises a clean-in-place flowpath assembly located in the dispenser and including a supply of cleaning or sanitizing fluid and a flowpath which is configured to deliver the cleaning or sanitizing fluid to or through the product flowpath.

As embodied herein and with reference to FIGS. 1 and 2, the sanitary manifold 200 in accordance with the invention includes milk manifold 230 and portions of the Clean-In-Place ("CIP") system. Portions of the CIP system include at least, for example, clean in place or "buffer" reservoir 980, valve 986 and caustic valve 987 connected to containers 986*a* and 987*a* containing cleaning or sanitizing fluid, CIP pump 988, hot water tank 751, and valves 750, 755, 945, 950, 955, and 989. However, the sanitary manifold 200 is not limited to these particular parts or the particular embodiments shown in the drawings. Any one of a variety of arrangements of valves, reservoirs etc. and flow lines can be used to dispense a food product and clean the system periodically in accordance with the invention. The CIP system may also be used for descaling purposes. In this case, a container of acidic solution may be arranged with a control valve to supply the acidic solution to the system. The acidic solution may be provided in a concentrated form and diluted with water in the CIP reservoir 980. Once diluted by a sufficient amount, the solution may be circulated periodically through the dispenser to descale the surfaces of the CIP and product flowpaths.

With reference to FIG. 2, the milk manifold 230 is adapted for being selectively traversed and flushed by cleaning or sanitizing fluids such as hot water 820, steam and chemical sanitizing agents coming from cleaning line 703 or sanitizing line 704. The selection and opening of the cleaning line 703 or sanitizing line 704 can be made by means of valves 705, 706 controlled by controller 1000 (See FIGS. 1 and 2). Typically, for milk-based concentrates, the sanitizing agents will be chosen from among the group including caustic soda, low foaming dishwater solutions, or chlorinated or phenylated solutions. The cleaning fluid may also encompass descaling agents such as acid solutions.

Figure 6:
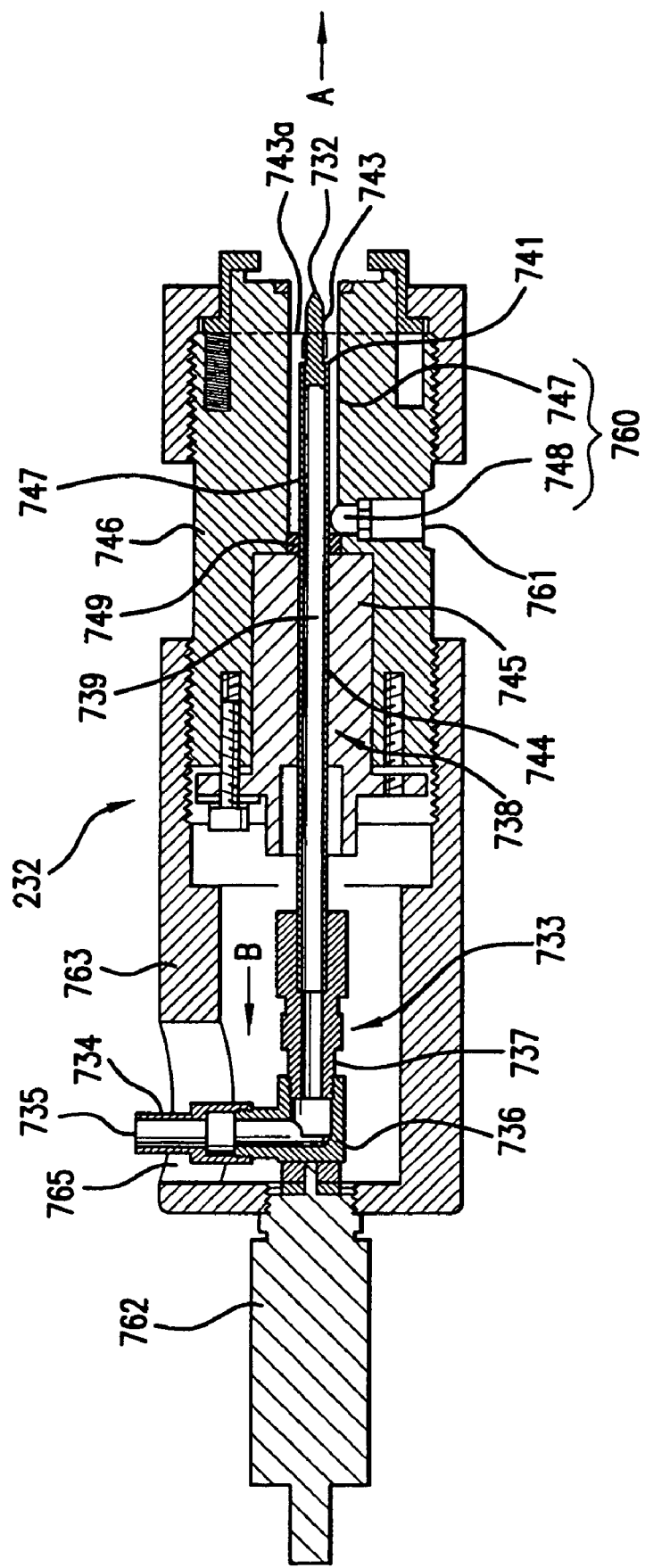
FIG. 6 is a partial schematic representation of the automated food product dispenser of FIG. 1 showing a cross-sectional view of the milk manifold.

As embodied herein and with reference to FIGS. 2 and 6, the milk manifold 230 includes a housing 232 of substantially cylindrical shape. At a first end 231 of the housing 232 is provided an interface connection 233 adapted to receive in a removable manner the fitment 300 of the container assembly 210. The housing 232 has a hollow configuration with a central bore 744 to enable a moveable cleaning fluid line assembly 733 to be coaxially mounted within the central bore 744. The cleaning fluid line assembly 733 comprises a first connector 734 that defines an inlet 735 for the cleaning or sanitizing fluid to enter the milk manifold 230 at about 90 degrees relative to the longitudinal axis of the central bore 744. Connector 734 thus connects to a second intermediate L-shaped connecting part 736 of the line assembly that directs the flow of cleaning fluid along the longitudinal axis and connects itself to a third connecting part 737. The third connecting part 737 is attached to a projection member 738 that includes an axial conduit 739 for transporting the cleaning fluid up to a fluid port 741 located close to a terminal spear 743 of the projection member 738.

Figure 7:
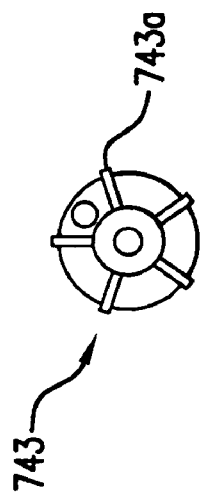
FIG. 7 is a partial schematic representation of the automated food product dispenser of FIG. 1 showing the tip of the spear.

The spear 743 has a sharp end 732 capable of cutting a membrane 350 (See FIG. 2) of the fitment 300 upon actuation of the projection member 738 forward in a reciprocating manner. Since the parts 734, 736, 737 738 and 743 are fixedly attached together, the whole line assembly 733 can reciprocate along the bore 744 of the housing 232. As illustrated in FIG. 7, the spear 743 preferably comprises a plurality of circumferentially oriented cutting splines 743*a* arranged to cut open the membrane 350 and provide a sufficiently wide opening in the fitment 300 for the flow of milk based fluid 211*a* to properly traverse the fitment 300 without retaining zones where solid deposits could easily settle. Furthermore, the splines 743*a* also play a role to direct the flow of cleaning fluid toward the fitment 300 and hose 212 of the container assembly 210.

As further embodied herein, a portion of the projection member 738 is closely guided in axial movement along the portion of bore 744 of an internal body 745 of the housing 232. The internal body 745 is attached by means of a connection means such as screws to a front body part 746. The front body 746 comprises a chamber 747 of larger diameter than the external diameter of the projection member 738 so as to demarcate an annular room that extends inwardly from the interface connection 233 to a discharge conduit 748 positioned at right angle with respect to the chamber 747. The chamber 747 and discharge conduit 748 form together a discharge line 760 that terminates by a discharge outlet 761. A sealing gasket 749 is provided between the internal body 745 and the projection member 738 to make the discharge line 760 inwardly watertight.

Figure 8:
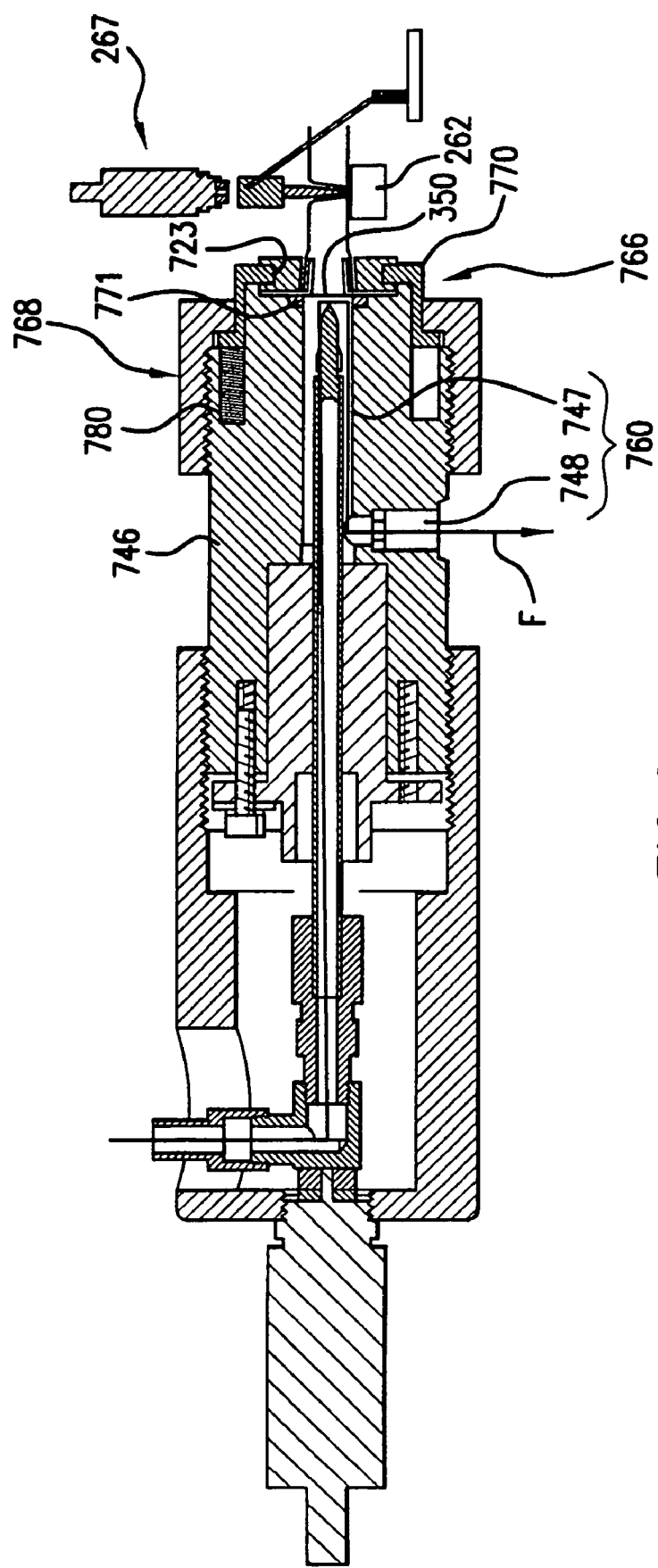
FIG. 8 is a partial schematic representation of the automated food product dispenser of FIG. 1 showing a cross sectional view of the milk manifold and a fitmented hose of a milk container assembly connected thereto.

In the rear end of the housing 232 an actuator 762 is provided, preferably an electromagnetic solenoid actuator coaxially mounted on a rear hollow body part 763 of the housing 232. The actuator 762 is mounted in engagement with the cleaning fluid line assembly, more particularly to the second connector 736. The actuator 762 can be of a push-and-pull solenoid type. Thus, in response to a control signal originating from a control circuit (not shown), the actuator pushes on the fluid line assembly 733, in the direction of arrow A as shown in FIG. 6, which has the effect to move the projection member 738 and its spear 743 forward in an inserted position in which the tip of the spear 743 extends beyond the interface connection 233. When the actuator 762 is de-energized, the projection member 738 stops in the inserted position. When the actuator 762 is energized again, it tends to push the line assembly 733 back in a retracted position, i.e., in the direction of arrow B, in which the spear 743 is located in a position inset relative to the interface connection 233. It can noted that the actuator 762 could also be of a push type only and combined with a return spring inserted between body part 745 and the connector that pushes the projection member 738 back in retracted position upon de-energization of the solenoid (not shown). As shown in FIG. 6, the rear body part 763 of the housing 232 comprises an elongated orifice 765 of a shape and size adapted for the inlet and connectors 734, 735 to move axially as an integral part of the whole fluid line assembly. Of course, the solenoid actuator 762 could also be replaced by equivalent actuating means such as a cam mechanism, a worm gear or a rack and pinion system (not shown). As illustrated in FIG. 8, the milk manifold 230 comprises coupling means that complementary engages a terminal fitment 300 of the container assembly 210. The configuration of the coupling means may widely vary depending upon the type and shape of the fitment 300 to be locked in place. The coupling means should be able to provide a watertight connection at the interface connection 233 in order to establish a reliable and secure fluid communication between the portion of hose 212 and the dispensing line 620 of the manifold system 230 and avoid risks of fluid leakage outside the system. In a preferred mode, as shown in FIG. 8, there is provided a spring loaded holder 766 having a ring shaped lip 770 adapted to engage a complementarily shaped annular groove 723 of the fitment 300. The fitment 300 is so urged in abutting contact with the end surface of housing 232 against a seal 771 placed at the periphery of the interface connection 233 by means of a retaining nut 768 that progressively forces on the holder 766 upon screwing on a portion of the body part 746 of the housing 232. Some elasticity is given on the holder 766 to avoid permanent deformation of the elements and compensates for backlash by a spring or other elastic means 780 that is inserted between holder 766 and body part 746.

It is clear the connection between the fitment and the manifold system could be carried out by other equivalent mechanical means such as by a cam type mechanism or a lever type mechanism to provide the same result without departing from the spirit of the invention. It is also clear that the receiving means of the fitment could also be formed from a protruding part as opposed to an annular groove and the holder formed from a recess instead of an annular lip wherein the protruding part of the fitment would complementary fit the recess of the holder.

Figure 9:
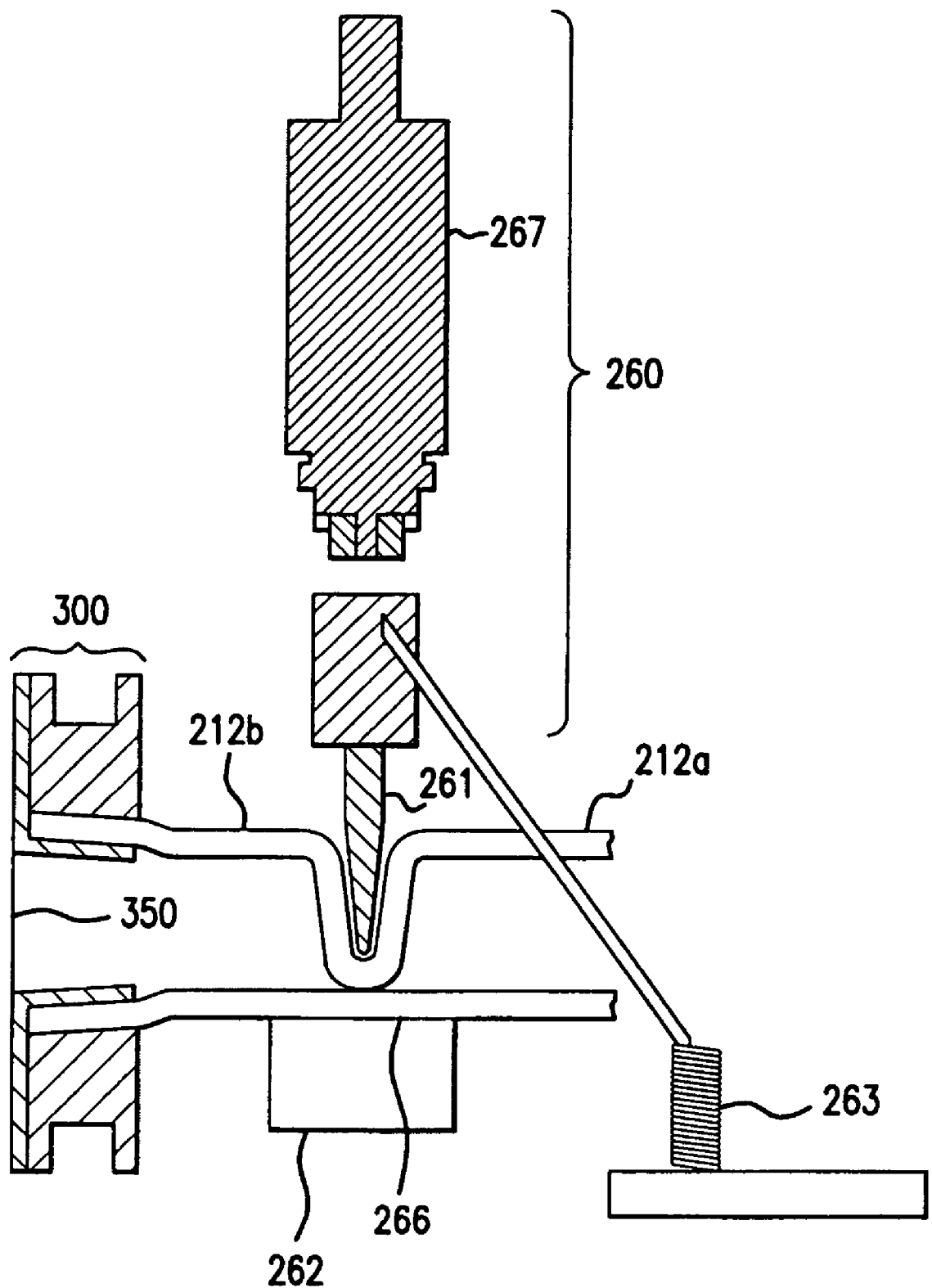
FIG. 9 is a partial schematic representation of the automated food product dispenser of FIG. 1 showing the fitment and hose of the milk container assembly and pinch valve of the dispenser.

Referring to FIGS. 2 and 9, the manifold system 230 further comprises an external valve that is preferably situated as close as possible to the interface connection 233 and that externally engages the portion of hose 212 of the container assembly 210. The external valve is preferably a spring loaded pinch valve 260 with a pinching member 261, a pinch block 262 and a tension spring 263. The tension spring 263 constantly maintains a certain closing pressure of the pinching member 261 at a pinch point 266 on the hose and against the pinch block 262. Due to the tension of the tension spring 263, the valve 260 acts passively in a rest configuration. The pressure exerted by the valve 260 is typically sufficient to hermetically close the hose 212 at the pinch point 266 when the pump 203 is not in action. Hence, the portion of hose 212 situated upstream the pinch point 266 can be maintained sterile in this rest situation. When the pump 203 is acting, the pressure exerted by the flow of the concentrate in the upstream part 212a of the hose 212 is sufficient to overcome the threshold tension value of the tension spring 263 and therefore to force the pinch valve 260 to open.

By virtue of the flow force created and direction of the flow, microbial substances can not attain the upstream portion of hose which remains sterile. In a cleaning situation where the cleaning or sanitizing fluid is pushed under pressure from the manifold system 230 within the fitment 300 and the downstream portion 212b of hose 212, the threshold tension of the pinch valve 260 can be raised to a higher value by pinch actuator 267 that exerts an additional pressure adding to the spring tension on the pinching member 261. Therefore, the threshold tension of the valve 260 is increased sufficiently above the cleaning fluid pressure to ensure that no cleaning or sanitizing fluid can enter the sterile portion of the container assembly 210. Therefore, in all conditions, the portion 212a of hose 212 past the pinch point 266 can remain safely sterile while the portion 212b of hose 212 prior the pinch point 266, which is no more sterile after breaking of the membrane 350, can be periodically cleaned and rinsed. As a result, the delivery conditions of the microbiologically sensitive fluid, e.g., milk concentrate, are safely controlled and refrigeration in the dispensing unit 100 is not necessary.

Referring again to FIG. 8, the cleaning operation will now be discussed when a new container assembly 210 is put in place and attached to the milk manifold 230. Since the container assembly 210 comprises external parts of the fitment and of the membrane 350 which can readily not be maintained sterile and which interface with the dispensing line 620 after the fitment 300 has been coupled to the coupling means of the manifold system 230, a preliminary cleaning operating mode is preferably carried out for each new container assembly 210 to prevent immediate contamination of the dispensing line 620 when a new container assembly 210 is put in place.

Further details regarding the milk manifold 230 and sanitary manifold 200 is described in co-pending U.S. patent application Ser. No. 10/187,939 by Peter W. Carhuff et al. filed Jun. 28, 2002 entitled "SANITARY MANIFOLD SYSTEM AND METHOD FOR HYGIENICALLY DISPENSING FLUIDS" which, is incorporated herein by reference in its entirety.

In further accordance with the invention, an automated food product dispenser is provided wherein the interface connection is adapted to engage the milk based fluid reservoir wherein the milk based fluid reservoir includes a flexible hose portion and a fitment.

Figure 10:
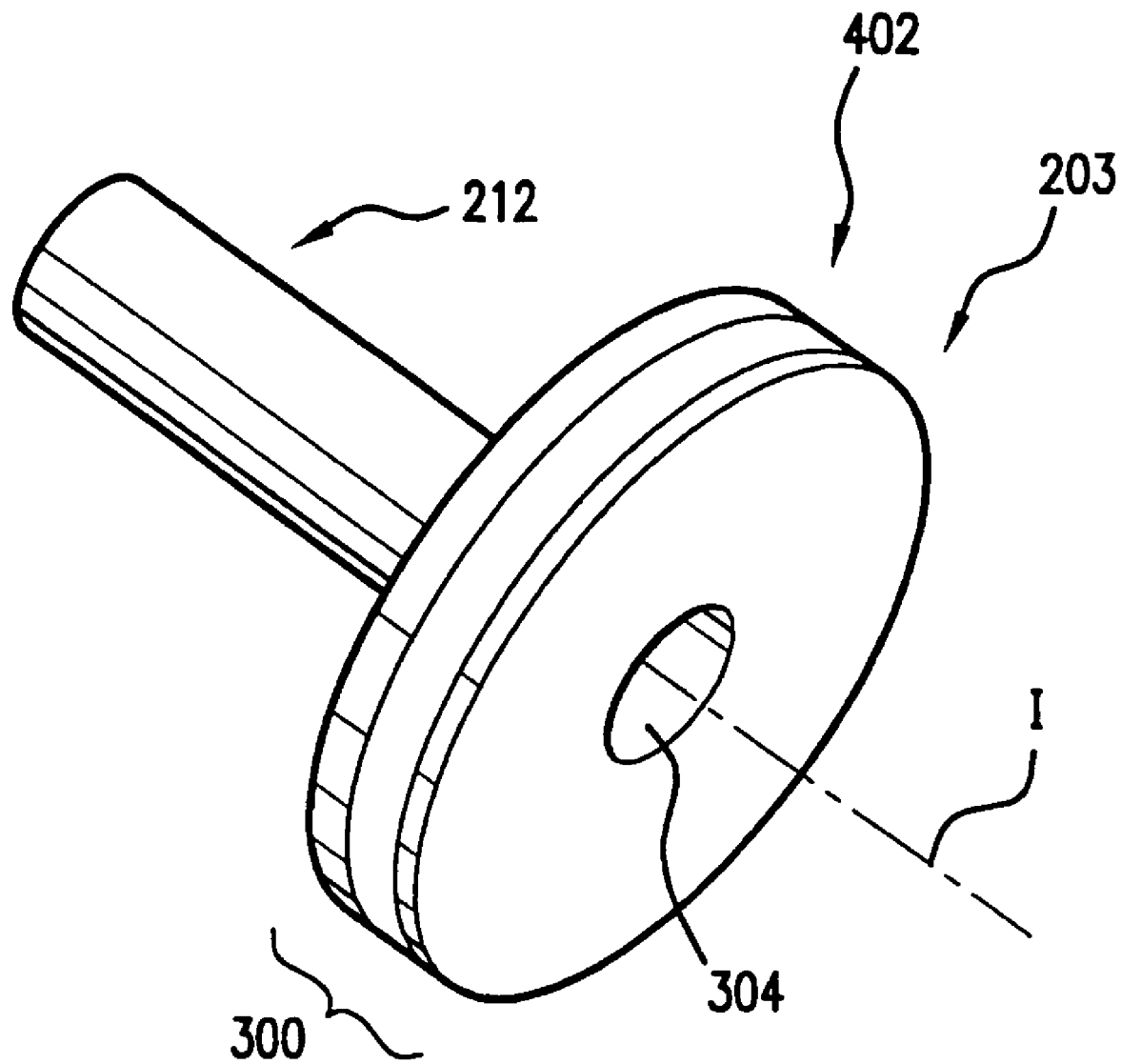
FIGS. 10-12 are partial schematic representations of the automated food product dispenser of FIG. 1 showing the fitment in accordance with the invention.
Figure 11:
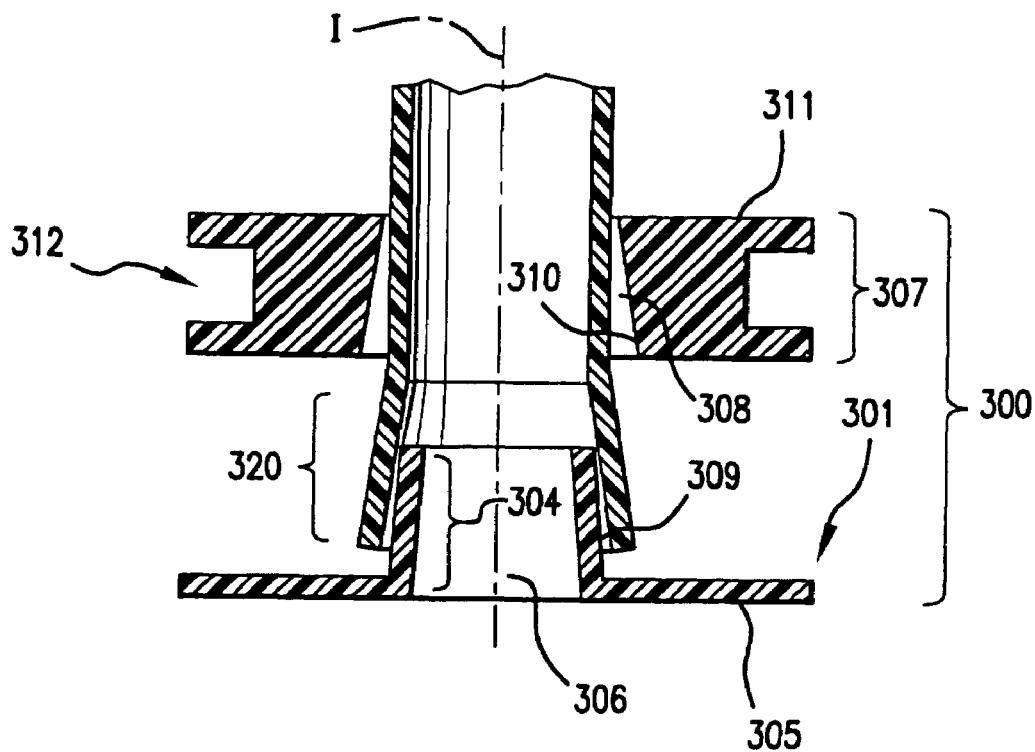
Figure 12:
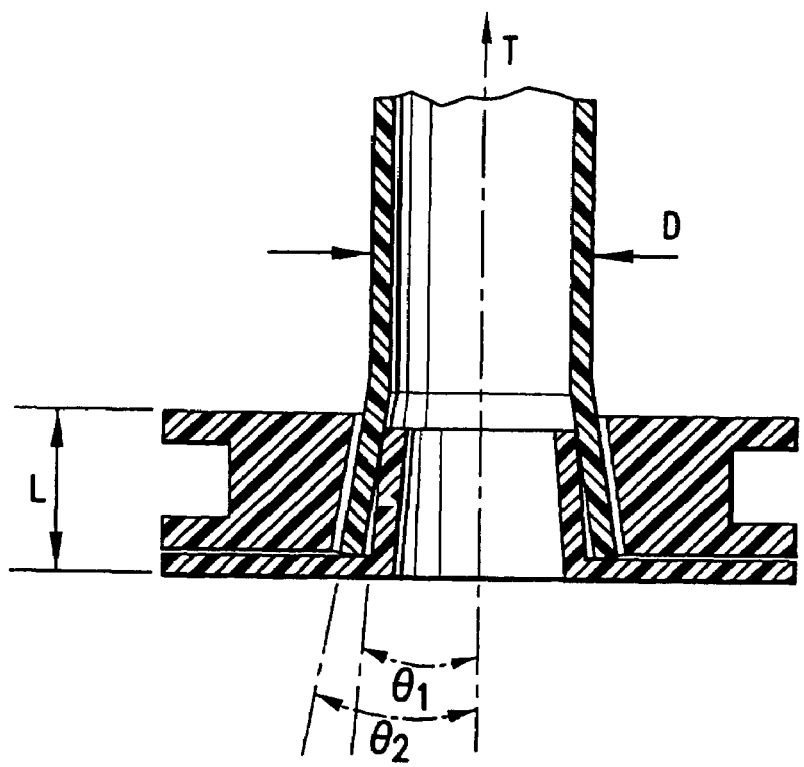
Figure 13:
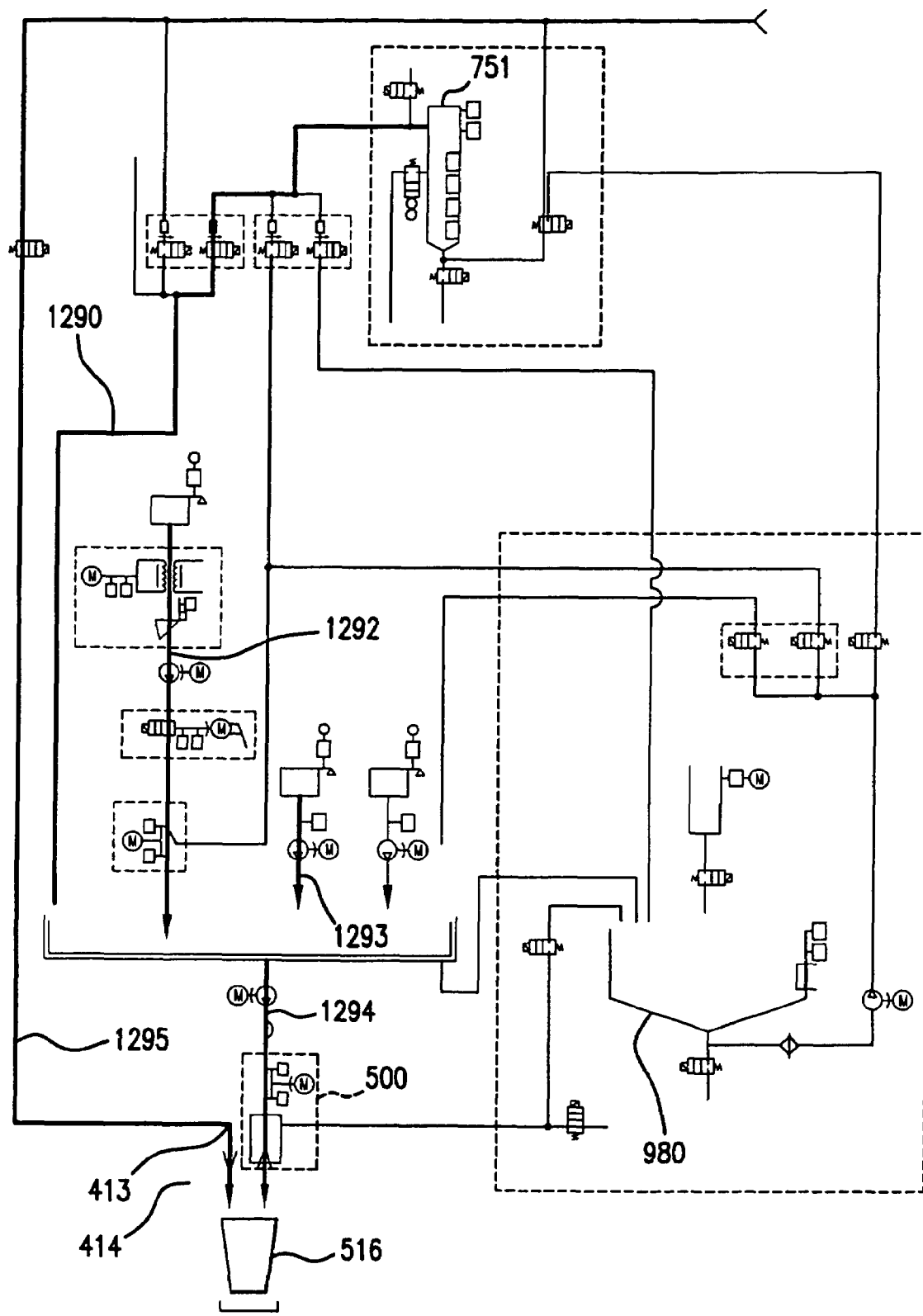
FIG. 13 is a schematic representation of the automated food product dispenser of FIG. 1 showing flowpaths that are active during a cappuccino/latte dispensing operation.

As embodied herein and with reference to FIGS. 10 to 12, the fitment 300 is composed of two main pieces, namely a first body member 301 and a ring-shaped sleeve 302 which when assembled and secured together to a terminal part or end 303 of hose 212 form a fluid tight assembly between the fitment 300 and the hose 212.

As shown in FIG. 11, the first body member 301 of the fitment 300 includes a portion of tube or socket 304 that extends along a longitudinal axis I. The socket 304 forms a tubular engaging surface with an external section that is configured to engage with the internal diameter of the hose 212. Preferably, hose 212 is made of resilient plastic material that slightly stretches to fit snugly onto socket 304. A terminal abutting wall 305 is provided at a first end of the socket 304 that demarcates a central fluid inlet 306 of axis I. When the hose 212 is fitted onto socket 304, the hose 212 abuts abutting wall 305.

The fitment further comprises a second member 307 that is a sleeve preferably having the form of a ring with an internal bore 308 forming a second engaging surface with the hose end. The bore of the sleeve 307 is adapted to snuggly engage the external surface of the hose end so as to create a fluid tight connection as shown in FIG. 12. More particularly, the socket 304 and bore 308 have differing surface shapes arranged to form wedging on the end of hose 212 so that hose 212 can resist disengagement upon pulling. In a preferred embodiment, socket 304 possesses an engaging surface 309 that progressively tapers in the direction of hose 212 to form an inclination $\theta_1$ with respect to the longitudinal axis I. Similarly, bore 308 has an engaging surface 310 that progressively tapers in the same direction but at an inclination $\theta_2$ that is greater than $\theta_1$ so as to create a wedge area 320 that pinches hose 212 proximate the external radial surface 311 of the sleeve 307. Hence, hose 212 is properly secured between socket 304 and sleeve 307 while it resists a pulling force in a longitudinal direction defined by "T". Sleeve 307 further supports a coupling means 312 configured to engage with a retaining means of a dispensing line. When fitment 300 is secured to a dispensing line by the coupling means 312, a longitudinal force applied to hose 212 in a direction T results in sleeve 307 tightening down even more on hose 212, thereby holding hose 212 in place within fitment 300. The external diameter D of hose may be, for example, usually of about 1 to 1.5 cm; whereas the fitment length L may usually vary from about 0.5 to 1.2 cm. Excellent results have been obtained with a D of 1.2 cm and a L of 0.8 cm. The fitment is preferably made of food grade plastic such as polyolefins, polyamides, polystyrenes or tetrafluoropolyethylenes. Further details regarding the fitment and the manner in which it interacts with the manifold is described in co-pending U.S. patent application Ser. No. 10/187,941 by Peter W. Carhuff filed Jun. 28, 2002 entitled "HOSE FITMENT FOR DISPOSABLE FOOD CONTAINER" which, is incorporated herein by reference in its entirety.

The invention also provides for different methods of using a dispenser in accordance with the invention. The most preferred embodiments of these methods are presented in the following Examples.

The invention also provides for a computer program in machine readable format containing instructions to operate a dispenser in accordance with the invention. The computer program may be embodied either in software or in hardware, such as a memory chip. The computer program may be written using well known techniques as is well known in the art and converted into machine code. The computer program in accordance with the invention has instructions therein for operating the dispenser. Preferably, the instructions in machine readable format will be contained on a computer chip in the dispenser 100 for controller 1000 to access when control panel is operated by an operator. Thus, when an operator presses a button on control panel 1100 to make a milk-based beverage or perform a cleaning operation, for example, the computer chip containing the instructions in machine readable format will be accessed by the controller to operate the dispenser 100. However, the computer program may also be embodied in a software program and run from a computer located inside or outside of the device.

Also, the machine readable program may be configured so that cleaning operations can be performed automatically in accordance with the invention during specified time intervals. The machine readable program may thus be configured to operate in conjunction with a timer to carry out periodic operations. In the Examples below, it is preferred that controller 1000 perform all of the actions in operating the device unless it is specified that an operator is to perform a task. However, the invention is not so limited. An operator could perform any of the operations (such as opening or closing a valve) manually as is dictated by the convenience and needs of the operator. Furthermore, controller 1000 need not be physically embodied in control panel 1100. Controller 1000 is preferably located inside dispenser 100, but may also be located outside of dispenser 100.

EXAMPLES

The following examples are provided to illustrate preferred operating modes of the automated food dispenser in accordance with the invention. Each of these operating modes is for exemplary purposes only, and in no way are intended to limit the scope of the invention.

Example I

New Reservoir Connection

For purposes of illustration only, and with reference to FIGS. 1-3, an operating mode of the automated food dispenser in accordance with the invention will now be illustrated wherein a new reservoir 211 will be installed to replace an empty one.

In this example, reservoir 211 is to be replaced by an operator. As embodied herein, a machine operator presses a button 1110 on control panel 1100 to indicate that the reservoir 211 will be replaced. Pinch valve 216 then is opened. In this embodiment a second pinch valve 260 is spring loaded by tension spring 263 and is opened manually by pulling the pinching member 261 away from the pinch block 262 to allow the hose 212 and reservoir 211 to be removed.

An actuator 762 on milk manifold 230 is then energized, moving projection member 738 and spear 743 backward, away from the fitment 300 area. When the spear 743 has retracted, the actuator 762 is de-energized. Electromagnetic actuator 544 of the dispense nozzle 500 then is energized, bringing the dispenser nozzle 500 to the cleaning or sanitizing position. Once the nozzle 500 is in this position, the actuator 544 is de-energized.

Next, fitment 301 (with membrane 350 intact) on the end of hose 212 is then slid into the holder 766 on the milk manifold 230 of the dispenser 100. The holder 766 is closed manually by twisting a retaining nut 768, clamping down on the fitment 300 and pulling it snug against the manifold 230. The tubing from the reservoir assembly 210 is threaded into the pinch valves 260 and 216 as well as the supply peristaltic pump 203.

Hot water valve 750 then is opened, allowing hot water 820 to flow through projection member 738 of the manifold 230, across the face of the fitment membrane 350, into the mixing bowl 406. The whipper 409 is turned on and drain valve 930 is opened, forcing hot water 820 to flow through the whipper 406, nozzle 500, and to the drain 940 through the drain valve 930. Hot water 820 should now be flowing from the hot water supply valve 750 all the way through the system to drain through valve 930, sanitizing the flowpath that it traverses.

This begins sanitization of the milk supply and product area, including the membrane 350 on the fitment 300. The membrane 350 is still intact. This sanitizing flow of hot water 820 will preferably continue for a predetermined time, preferably about 1 minute. After the predetermined time has elapsed, valve 750 is closed. Shortly thereafter, preferably on the order of several second later, whipper 409 shuts off. Valve 930 then is closed. Actuator 544 then is energized again, bringing the dispenser nozzle 500 back to the dispensing position, and then is de-energized. This is followed by the closing of pinch valve 216. Next, actuator 762 is energized, pushing projection member 738 with spear 743 against the fitment 300 and punctures membrane 350. Actuator 762 then is de-energized. After a short delay, preferably on the order of a second, actuator 762 again is energized, moving the projection member 738 with spear 743 back away from the fitment 300 area. Once the spear 743 is in this position, the actuator 762 is de-energized. At this point, the reservoir 211 has been replaced and its contents are ready for dispensing, discussed in detail in Example II below.

Example II

Product Dispensing

For purposes of illustration only, and with reference to FIGS. 1-3 and 13, an operating mode of the automated food dispenser in accordance with the invention will now be illustrated wherein food product is dispensed by the dispenser.

In this example, the dispenser is operated by an operator to dispense a milk-based cappuccino drink food product. As embodied herein, a machine operator presses a button 1120 for cappuccino on the control panel 1100 as the product selection. In response to the command, controller 1000 opens valve 216 and is turned on peristaltic pump 203 to begin flow of milk based fluid 211a. The pressure generated by the pump 203 forces milk based fluid 211a past the spring loaded pinch valve 260.

Next, controller opens hot water supply valve 950 to begin a flow of hot water 820. Hot water 820 flows through water feed line 960 and milk based fluid 211a begins to flow through dispensing line 620 to the mixing bowl 406, where they begin to mix. The flowpath of milk based fluid 211a is signified by flowpath 1292 in FIG. 13 while the flowpath of hot water 820 is indicated by flowpath 1290. Controller 1000 then is turned on whipper 409. As they mix, the milk based fluid 211a and hot water 820 flow downward from mixing bowl 406 into the whipper 409 where they are whipped together into a substantially uniform mixture, and finally flow through the dispensing nozzle 500 into the cup 516. This step occurs for a pre-determined period to achieve an adequate amount of milk mixture 211b. After this period, the milk pump 203 is turned off by controller 1000. Shortly thereafter, preferably on the order of a second, whipper 409 is turned off, and coffee pump 411 is turned on. At this point, coffee and hot water 820 flow into the mixing bowl 406, through the whipper 409 (which is not running at this point), and through the nozzle 500 and into the cup 516, for a pre-determined time to achieve dosage. The flowpath of coffee in this operation is indicated by flowpath 1293 in FIG. 13, and the flowpath of hot water 820 is indicated by flowpath 1290.

After the coffee dosage has been achieved, coffee pump 411 is turned off. After a small delay on the order of several seconds to obtain an adequate amount of hot water 820 necessary for the drink recipe, the hot water supply valve 950 is turned off. It should be noted that, adding the remainder of the hot water 820 after the milk mixture 211b and coffee have been added to cup 516 facilitates recovery of most of the milk mixture 211b and coffee from the product flowpath 600 of the system by washing the milk mixture 211b and coffee into the cup 516.

Next, showering valve 413 is turned on by controller 1000 for several seconds to send water 810 through spray nozzle 414. This flowpath is indicated by flowpath 1295 in FIG. 13. Spray nozzle 414 sprays the foam on the top of the cup, washes the top layer of foam to whiten it, and breaks larger bubbles and moistens the foam to improve its appearance. After a pre-determined time, showering valve 413 is turned off by controller 1000 to stop the spray. After a short delay, preferably on the order of a second, actuator 544 is turned on, moving the dispensing nozzle 500 into the cleaning and/or sanitizing position. When the nozzle 500 reaches that position, actuator 544 shuts off.

Figure 14:
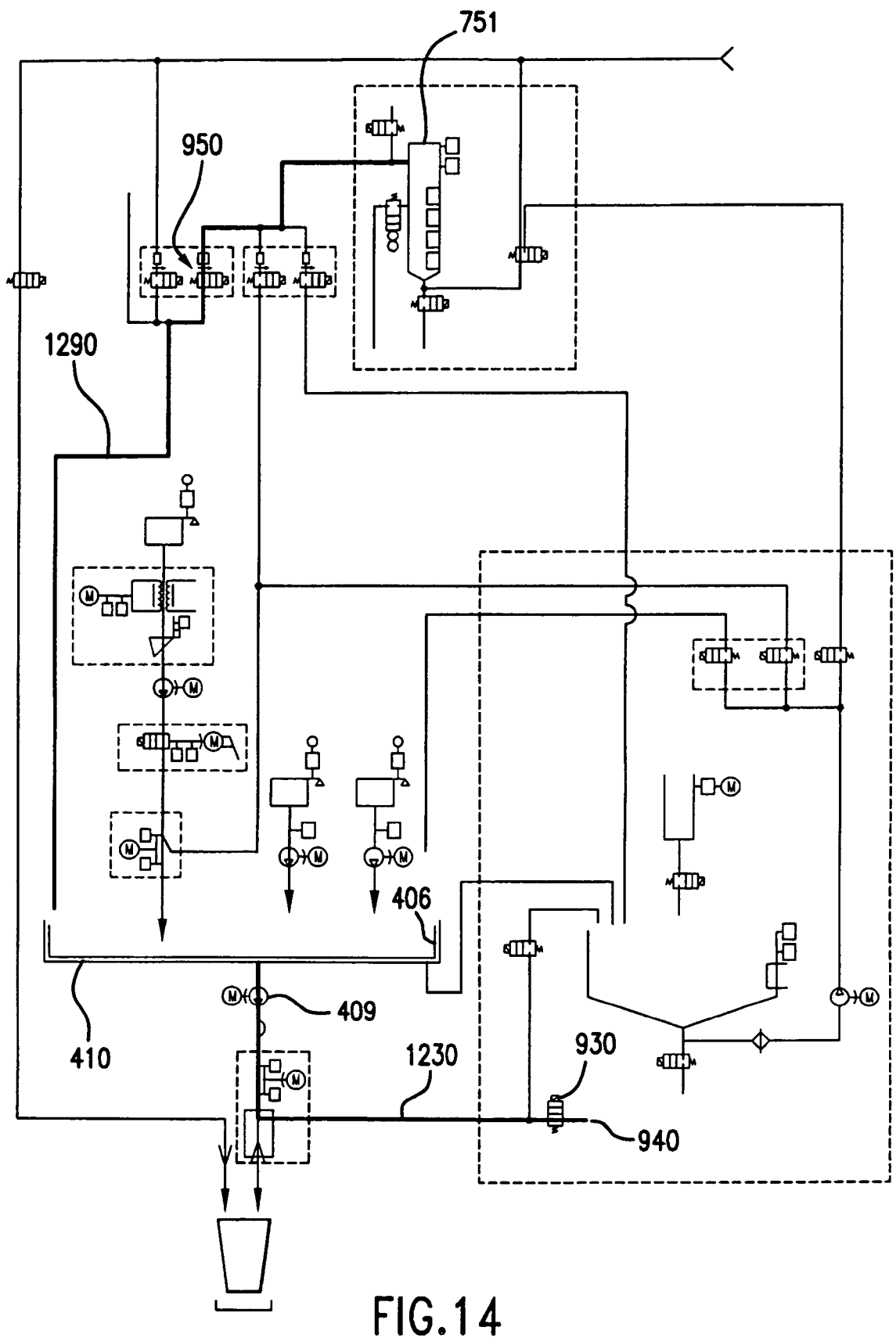
FIG. 14 is a schematic representation of the automated food product dispenser of FIG. 1 showing flowpaths that are active during a post drink dispensing rinse operation.

Next, hot water supply valve 950 is opened by controller 1000 to allow hot water 820 to flow into the mixing bowl 406. Whipper 409 is turned on at low speed, and drain valve 930 is opened. Hot water 820 flows through the mixing bowl 406, whipper 409, and dispensing nozzle 500 to rinse any residual food product from the system. The flowpath 1290 of the hot water 820 is shown in FIG. 14. The rinse goes to the drain 940 via valve 930. This hot water 820 also aids in maintaining system hygiene by rinsing and killing microorganisms that might be in the system. After a short delay preferably on the order of several seconds, hot water supply valve 950 is turned off. After several more seconds, whipper 409 is turned off and drain valve 930 is closed by controller 1000. Nozzle actuator 544 is then energized by the controller, moving the dispensing nozzle 500 to the dispensing position. When it has reached that position, actuator 544 is de-energized by the controller 1000.

Example III

Hygiene Maintenance

For purposes of illustration only, and with reference to FIGS. 1-3 and 6, an operating mode of the automated food dispenser in accordance with the invention will now be illustrated wherein the parts of the product flowpath 600 that including the dispensing line 620 and dispensing nozzle 500 are flushed periodically for purposes of hygienic maintenance. Controller 1000 can be programmed to perform this function at any specified interval. Preferably, such hygienic maintenance is performed after a pre-determined period of dispenser inactivity has been reached. For example, if the dispenser has not been used to dispense drinks for a period of time, such as one to two hours, the dispenser will then carry out a hygienic maintenance operation.

First, actuator 762 on the milk manifold 230 is energized, pushing the projection member 738 with spear 743 toward the fitment 300. The spear tip 743*a* will protrude into the fitment 300. Once the spear 743 is in this position, the actuator 762 is de-energized.

Next, pinch actuator 267 is energized, applying additional pressure on the spring loaded pinch valve 260 to ensure no leakage of hot water 820 through pinch valve 260 into the sterile milk area. Once the pinching member 261 has reached a pre-determined point (and therefore a predetermined closing pressure), the pinch actuator 267 is de-energized.

At this point, actuator 544 of the dispensing nozzle 500 is energized, bringing the dispenser nozzle 500 to the cleaning and/or sanitizing position. Once the nozzle 500 is in this position, the actuator 544 is de-energized. This is followed by opening hot water bypass valve 750, and drain valve 930. Hot water 820 now flows from the hot water tank 751, through valve 750, through the projection member 738 of the milk manifold 230, past the spear 743, into the region of fitment 300, through milk manifold 230, out through the sanitary manifold dispensing line 620, into the mixing bowl 406. The mixing bowl 406 fills up with hot water 820, which then over flows mixing bowl 406 and flows into the skirt 410, through overflow line 965, and into the drain 940 via drain valve 930. Pinch valve 260 stays closed in this exemplary operating mode, keeping hot water 820 from entering the hose 212 from the reservoir 211 and mixing with and contaminating milk based fluid 211*a* in the reservoir. Hot water 820 overflow of the mixing bowl continues for a pre-determined time, typically about 30 seconds and then stops.

After the hot water 820 overflow period ends, the whipper 409 is turned on, pumping hot water 820 from the mixing bowl 406 through the dispensing nozzle 500, and out to drain 940 via valve 930. This flow of hot water 820 preferably continues for a desired time interval, preferably one minute. At the end of that time interval, hot water supply valve 750 is closed. Shortly thereafter, preferably after a two second delay, the whipper 409 is turned off, and drain valve 930 is closed. Actuator 762 on the milk manifold 230 is energized, pulling the projection member 738 with spear 743 away from the fitment 300. Once the spear 743 is in its retracted position, the actuator 762 is de-energized. Nozzle actuator 544 then is energized, moving the dispensing nozzle 500 to its dispensing position. When dispensing nozzle 500 has reached its dispensing position, actuator 544 is de-energized.

Finally, pinch actuator 267 is energized, relieving the mechanical pressure added to the pinch valve 260 earlier. Valve 260 remains closed from pressure attributable only to the tension spring 263. Once the pinching member 261 has reached a pre-determined point, the pinch actuator 267 is de-energized. At this point, the operation is completer and the system has been rinsed and/or sanitized.

Example IV

Clean-in-Place

For purposes of illustration only, and with reference to FIGS. 1-3 and 6, an operating mode of the automated food dispenser in accordance with the invention will now be illustrated wherein the dispenser cleans itself using a cleaning or sanitizing liquid.

In this example, the controller 1000 of the dispenser 100 of the invention is programmed to automatically carry out a Clean-In-Place ("CIP") cycle. However, the invention is not so limited. A CIP cycle can also be initiated by an operator.

As embodied herein, controller 1000 begins the CIP cycle by opening hot water CIP valve 985, mixing bowl rinse valve 955, and shutoff valve 989, which are initially closed. Hot water 820 now flows from the hot water tank 751, through CIP valve 985 into the CIP reservoir 980. Pinch actuator 267 is energized, applying additional pressure on the pinch valve 260 to ensure no leakage of hot water 820 through the valve into the sterile milk area. Once the pinch has reached a pre-determined point (and therefore closing pressure), the pinch actuator 267 is de-energized.

Next, actuator 762 on the milk manifold 230 is energized, pushing the projection member 738 with spear 743 toward fitment 300. The spear tip 743*a* will protrude into the fitment 300. Once the spear 743 is in this position, the actuator 762 is de-energized.

Once the CIP reservoir 980 has filled (as indicated by a conductivity level sensor 982), CIP pump 988 is turned on, pumping hot water 820 through shutoff valve 989, mixing bowl rinse valve 955, and into the mixing bowl 406 via the water feed line 960 to the mixing bowl 406. The mixing bowl 406 fills up with hot water 820, which then over flows into skirt 410 and into the overflow line 965, and into the drain 940 via drain valve 930. Pinch valve 260 stays closed, keeping hot water 820 from entering the hose 212 from the reservoir 211 and mixing with (and contaminating) the milk based fluid 211*a* in the reservoir 211.

Next, the whipper 409 pulses on for short durations. A preferable cycle is having the whipper 409 turn on for ten seconds, followed by whipper 409 being turned off for ten seconds. While the whipper 409 is running, hot water 820 flows through the whipper 409 and the dispensing nozzle 500 rather than through the mixing bowl 406 and overflowing through skirt 410 and overflow line 965.

After a pre-determined period of time that is preferably about 1 minute, sanitary manifold 200 CIP valve 755 is opened, and the mixing bowl rinse valve 955 is closed. Rinsing now goes through the milk manifold 230. During this time, the whipper 409 continues to pulse on and off for short durations as described above.

After a pre-determined period that is preferably about one minute, the CIP pump 988 is turned off, the whipper 409 is turned off (and stops its intermittent pulsing), and drain valve 930 is closed. The hot water CIP valve 985 is then opened to refill the CIP reservoir 980 with hot water 820. Once the CIP reservoir 980 has been filled (as indicated by a conductivity level sensor 982), the caustic valve 987 is opened to permit caustic cleaner concentrate 984 to flow into the CIP reservoir 980 to make a caustic solution 984*a*. After a pre-determined period of time, caustic valve 987 is closed.

Next, CIP pump 988 is turned on, pumping hot caustic solution 984*a* from the CIP reservoir 980 through shutoff valve 989, through the milk manifold 230, and into the mixing bowl 406. The mixing bowl 406 fills up with caustic solution 984*a*. The caustic solution 984*a* then overflows mixing bowl 406 into skirt 410 and flows into the overflow line 965, and into the CIP reservoir 980 via the recirculation valve 970. Pinch valve 260 stays closed during this operation, keeping caustic solution 984*a* from entering the hose 212 from the reservoir 211 and mixing with and contaminating the milk based fluid 211*a*.

The whipper 409 again pulses on for short durations (e.g., cycles of turning on the whipper 409 for ten seconds followed by turning whipper 409 off for 10 seconds). While whipper 409 is running, caustic solution 984a flows through the whipper 409 and the dispensing nozzle 500 rather than overflowing mixing bowl 406 into skirt 410 and flowing through overflow line 965.

After a pre-determined period of time, preferably about three minutes, the CIP valve 755 is closed, and the mixing bowl rinse valve 955 is opened. Caustic solution 984a then flows through the water feed line 960 to the bowl 406. While the flow of caustic solution 984a occurs, whipper 409 continues to pulse on and off for short durations of time.

Next, after a pre-determined period of time, preferably about three minutes, the whipper 409 is turned on, preferably at a relatively low, constant speed, without pulsing, and drain valve 930 is opened while recirculation valve 970 is closed. This step pumps the caustic solution 984a from the CIP reservoir 980, through the system, and to the CIP drain 941 via CIP drain valve 981, to purge the bulk of the caustic solution 984a from the system. After a pre-determined period, preferably about one minute, the CIP pump 988 is turned off and the whipper 409 is turned off. Next, CIP reservoir drain valve 981 is opened to drain any remaining caustic solution 984a from the CIP reservoir 980. CIP reservoir drain valve 981 stays open for a relatively short time, preferably about 15 seconds.

At this point, hot water CIP valve 985 is opened to refill the CIP reservoir 980 with hot water 820. Once the CIP reservoir 980 has been filled with hot water 820 (as indicated by a conductivity level sensor 982), CIP pump 988 is turned on, pumping hot water 820 through shutoff valve 989, mixing bowl rinse valve 955, and into the mixing bowl 406 via water feed line 960. Alternatively, hot water could be supplied directly from hot water tank 751 to mixing bowl 406 by way of hot water supply valve 950.

The mixing bowl 406 is filled with hot water 820, which then over flows into skirt 410, into the overflow line 965, and into the drain 940 via drain valve 930. Pinch valve 260 stays closed, keeping hot water 820 from entering hose 212 from the reservoir 211 and mixing with and contaminating milk based fluid 211a. Whipper 409 then pulses on and off for short durations, preferably for about 10 seconds on and 10 seconds off. While the whipper 409 is running, flow goes through the whipper 409 and the dispensing nozzle 500 rather than through the mixing bowl overflow line 965.

After a pre-determined period, preferably about two minutes, CIP valve 755 is opened, and the mixing bowl rinse valve 955 is closed. Hot water 820 now goes through the milk manifold 230, rinsing it. After a pre-determined period, preferably about one minute, the whipper 409 is turned on, preferably at a steady, relatively slow speed. Water supply valves 945 and 950 turn on for a short duration, preferably about five seconds to rinse the valve ends. During this step, the rinse water 850 from the CIP reservoir 980 is pumped through the system, and through CIP drain valve 981 to CIP drain 941. Hot water 820 obtained directly from hot water tank 751 could also be run through the system for rinsing, rather than using the CIP pump 988 to pump rinse water 850 through the system.

Next, after a pre-determined period, preferably about one minute, the CIP pump 988 is turned off. The hot water bypass valve 750 is opened to allow further rinsing and hot water sanitization of the milk manifold 230, mixing bowl 406, whipper 409, and dispensing nozzle 500.

After another pre-determined period, preferably about one minute, the hot water bypass valve 750 is closed. After a short delay, preferably about two seconds, the whipper 409 is turned off, and drain valve 930 is closed. Actuator 762 on the milk manifold 230 is then energized, pulling the projection member 738 with spear 743 away from the fitment 300. Once the spear 743 is in its retracted position, the actuator 762 is de-energized. Nozzle actuator 544 is then energized, moving the dispensing nozzle 500 to the dispensing position. When nozzle 500 has reached its dispensing position, actuator 544 is de-energized. Valve 981 is then opened for a predetermined time, preferably fifteen seconds to drain any remaining rinse water 850 from the CIP reservoir 980 through CIP drain 941. At the end of the predetermined time, valve 981 and CIP shutoff valve 989 are closed.

Finally, pinch actuator 267 is energized, relieving the mechanical pressure added to the pinch valve 260 earlier. Pinch valve 260 remains closed from the pressure attributable to tension spring 263 only. Once the pinching member 261 has reached a pre-determined point, the pinch actuator 267 is de-energized. At this point, the exemplary system CIP cycle is complete.

Example V

Reservoir Removal

For purposes of illustration only, and with reference to FIGS. 1-3, an operating mode of the automated food dispenser in accordance with the invention will now be illustrated wherein the reservoir assembly 210, as embodied herein, is removed by an operator.

To begin this procedure, the machine operator presses a button 1130 on the control panel 1100 to indicate the currently loaded reservoir assembly 210 is to be removed. In response to this operator input, controller 1000 energizes pinch actuator 267, which applies additional pressure on the pinch valve 260 by moving pinching member toward 211, compressing it. Once the pinching member 261 has reached a pre-determined point (and therefore closing pressure), the pinch actuator 267 is de-energized.

Next, heating element 290 is turned on by controller 1000, for a pre-determined period of time, preferably about thirty seconds to melt shut hose 212. The heating element 290 is then turned off. Hose 212 is now heat sealed, rendering the reservoir 211 unusable, and preventing any milk based fluid 211a remaining in the reservoir 211 from leaking out onto the operator or other components of dispenser 100.

Next, pinch actuator 267 is energized to move pinching member 261 backward from hose 212, thus relieving the mechanical pressure added to the pinch valve 260 earlier. Valve 260 remains closed from the pressure from tension spring 263 only. Once the pinching member 261 has reached a pre-determined point, the pinch actuator 267 is de-energized. Valve 216 is then opened.

The operator next opens the milk manifold 230 retaining nut 768 manually by lifting a lever. The fitment 300 on the end of the hose 212 is slid out of engagement with the holder 766 on the milk manifold 230 of the dispenser 100. The tubing from the reservoir 211 is unthreaded from the pinch valves 260 & 216 as well as the supply peristaltic pump 203. At this point, the dispenser 100 is ready for a new milk bag.

Example VI

Daily Hot Water Sanitization

Figure 15:
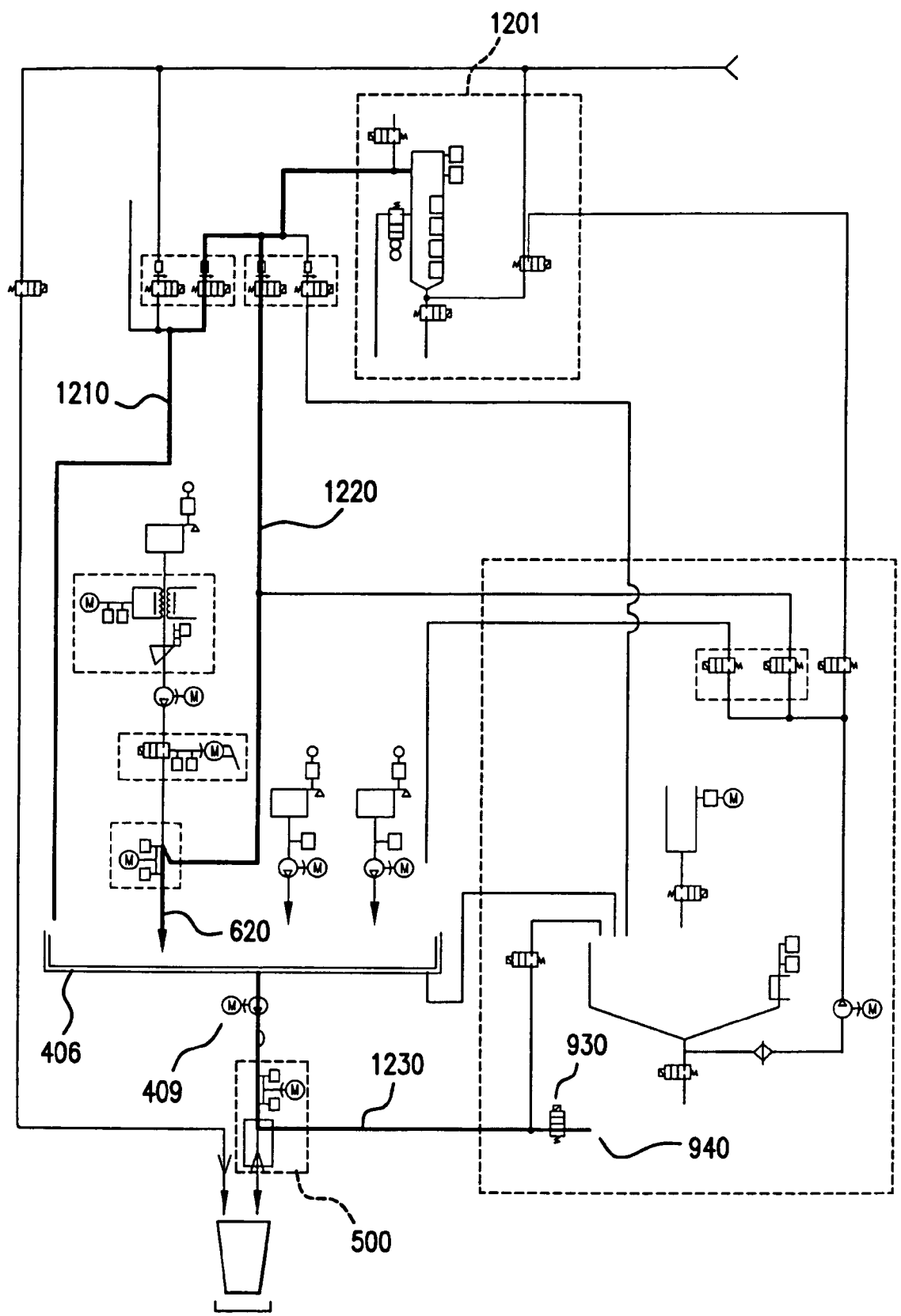
FIG. 15 is a schematic representation of the automated food product dispenser of FIG. 1 showing flowpaths that are active during a daily hot water sanitization operation.
Figure 16:
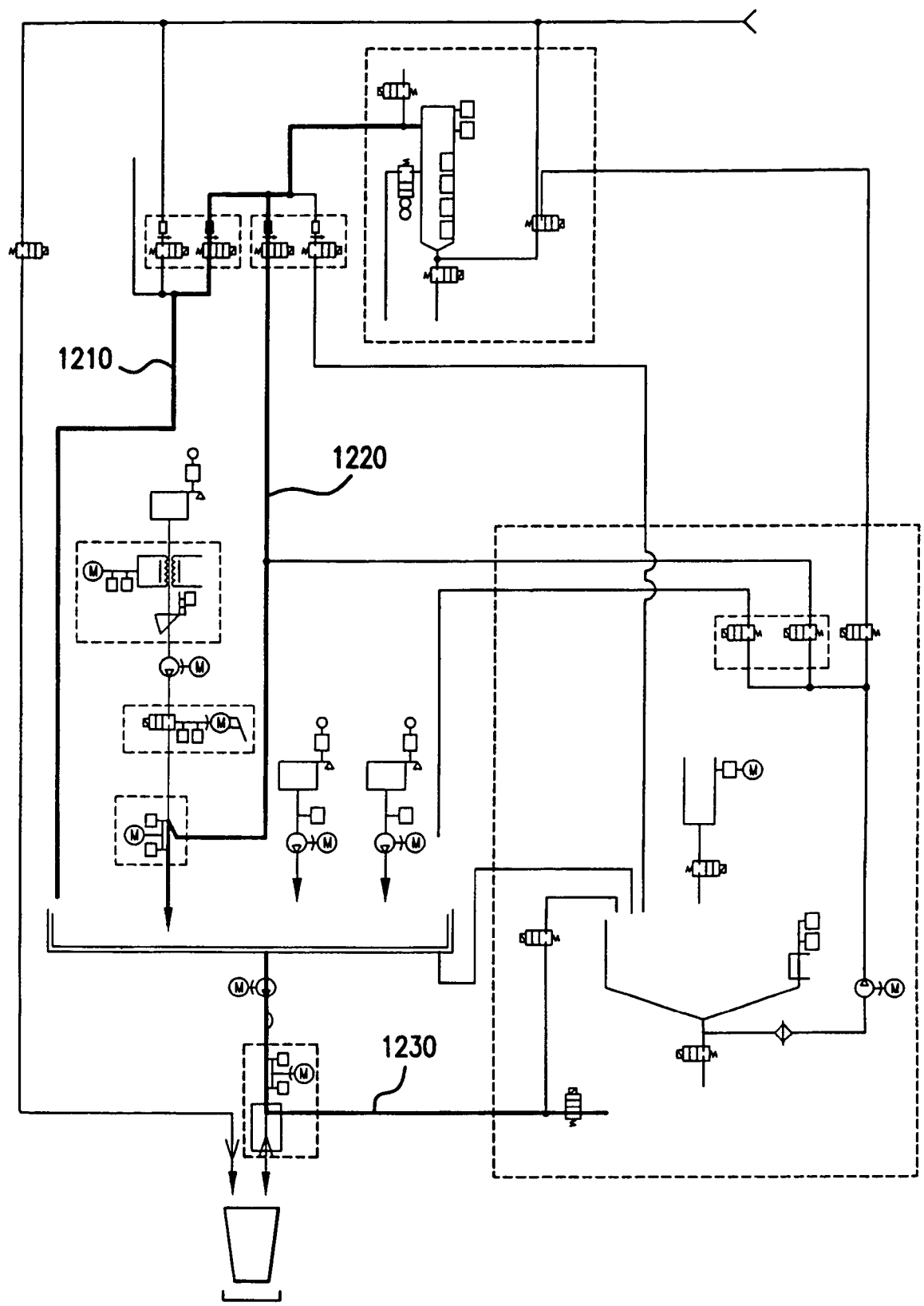
FIG. 16 is a schematic representation of the automated food product dispenser of FIG. 1 showing flowpaths that are active during a daily CIP initial rinse operation.

An additional schematic showing flowpaths for hot water 820 flow in an additional exemplary embodiment of a daily hot water sanitizing flowpath through dispenser 100 in FIGS. 15 and 16. As embodied in FIG. 15, flowpath 1210 is established to direct hot water from hot water supply module 1201 (containing hot water tank 751, not shown) to mixing bowl 406. Flowpath 1220 is similarly established between water supply module 1201 and milk manifold 230. Hot water 820 flows through milk manifold 230, out through dispensing line 620 into mixing bowl 406. Hot water 820 from flowpaths 1210 and 1220 mix together in mixing bowl 406, and flow down through whipper 409 running at a low speed setting, and through nozzle 500 in its cleaning and/or sanitizing position to drain 940 via drain valve 930, thereby forming flowpath 1230. While this operation is ongoing, pinch actuator 267 is pressing pinching member 261 against pinch block 262 with a preselected force thereby holding hose 212 shut with a preselected pressure to prevent hot water 820 from contaminating milk based fluid 211*a* in reservoir 211. As indicated in FIG. 16, this operation may be done on a daily basis.

Example VII

Other Daily and Periodic Operations

Variations of the operations described above can be carried out on dispenser 100 in accordance with the invention on a daily or other basis.

Example VII-A

Draining CIP Reservoir

Figure 17:
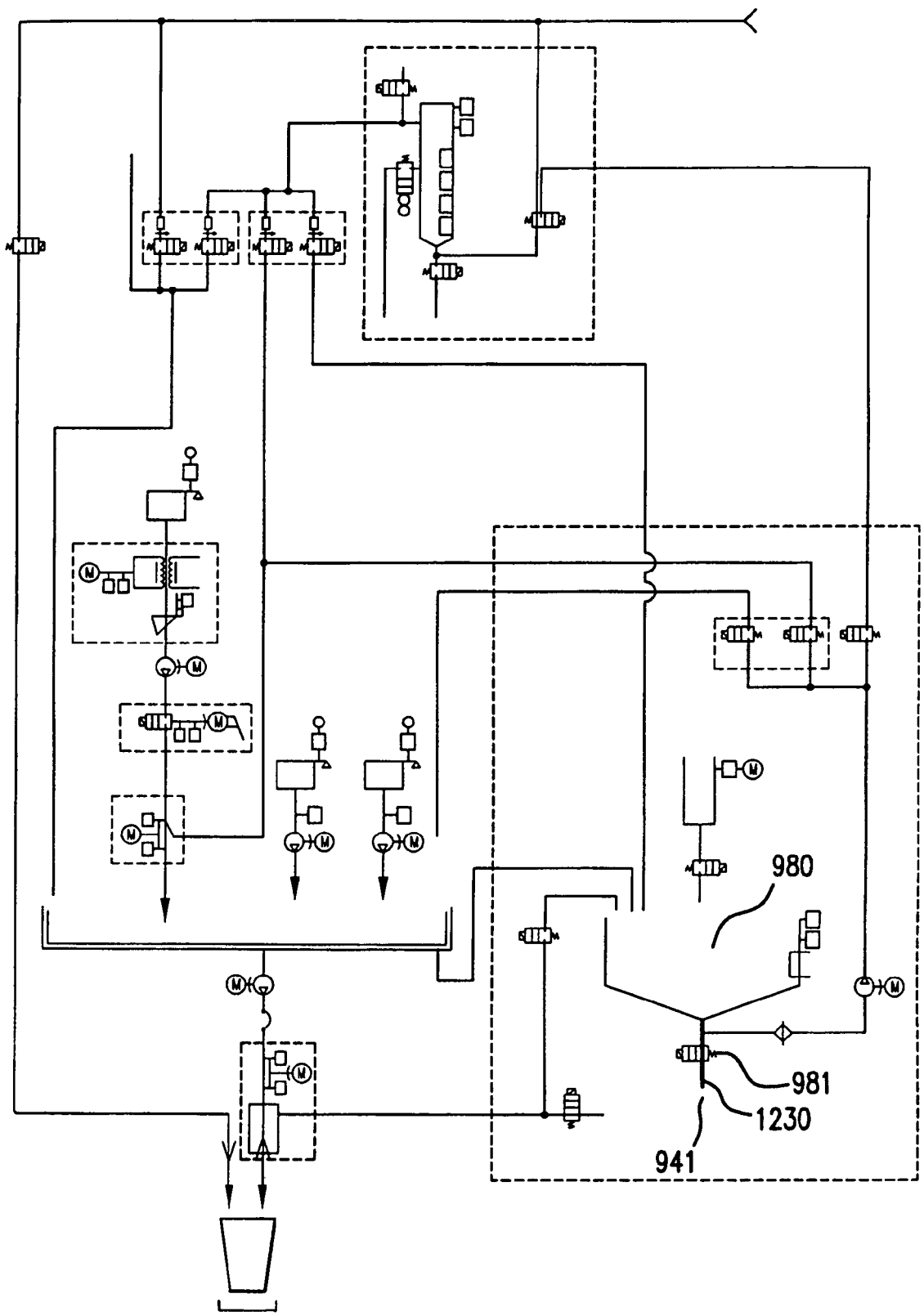
FIG. 17 is a schematic representation of the automated food product dispenser of FIG. 1 showing flowpaths that are active during a CIP reservoir draining operation.

For example, the flowpath 1230 established through CIP drain valve 981 is illustrated in FIG. 17. As embodied herein, in further accordance with the invention, the CIP reservoir 980 is be drained on a daily basis. When the CIP reservoir 980 is being drained, the CIP resistive heaters 990 and whipper 409 are preferably off and pinch actuator 267 is pressing pinching member 261 against pinch block 262 with a preselected force thereby holding hose 212 shut with a preselected pressure.

Example VII-B

Circulation Cleaning Loop for Mixing Bowl

Figure 18:
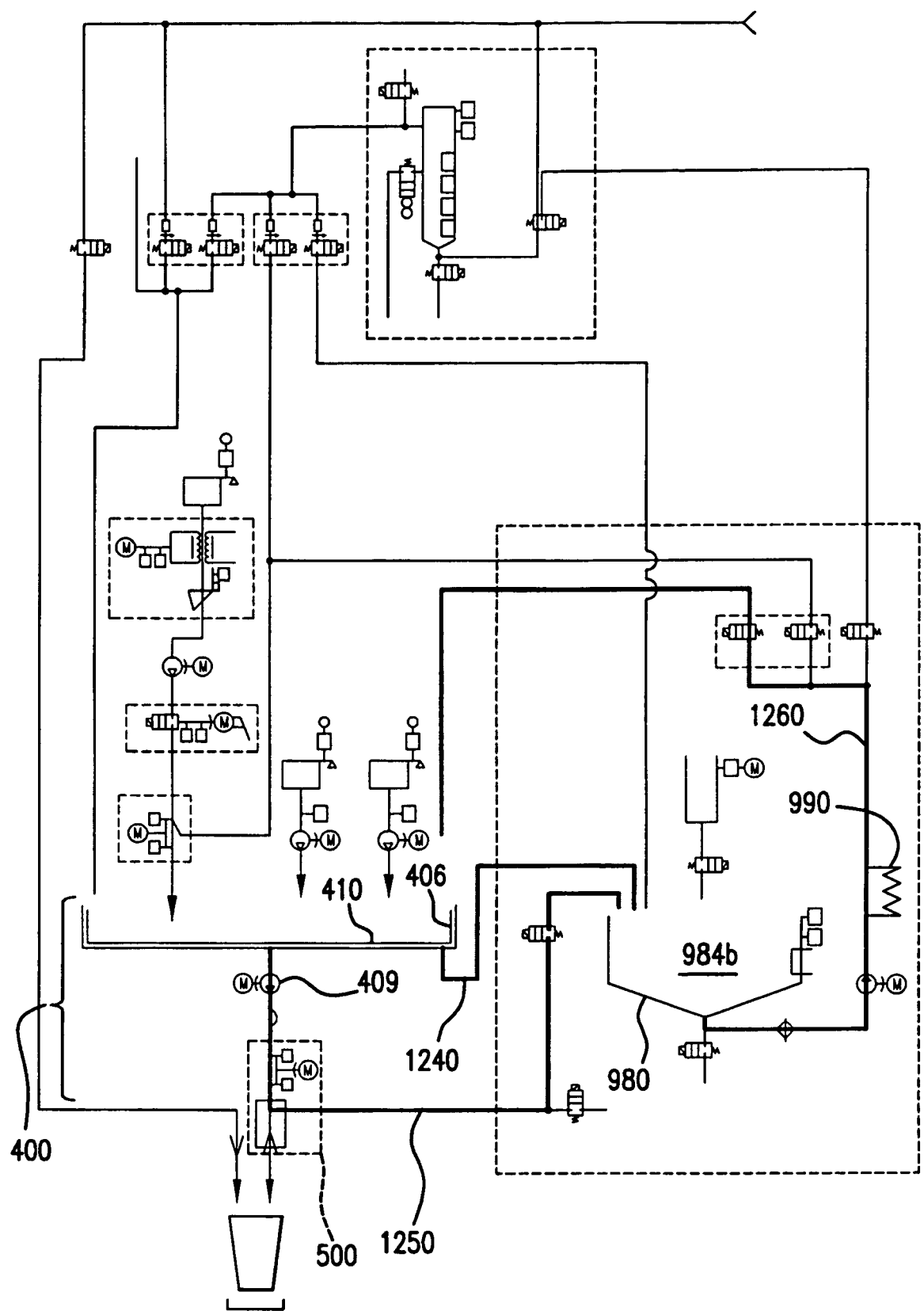
FIG. 18 is a schematic representation of the automated food product dispenser of FIG. 1 showing flowpaths that are active during a circulation cleaning loop operation for cleaning the mixing bowl and nozzle.

Similarly, FIG. 18 shows an additional exemplary embodiment wherein flowpaths 1240, 1250 and 1260 are established on a daily basis as a recirculation cleaning loop for mixing bowl 406. As embodied herein, flowpath 1260 is established by CIP pump 988 being turned on along with CIP resistive heaters 990. This causes the cleaning or sanitizing fluid 984*b* in CIP reservoir 980 to become heated and flow into mixing bowl 406. The cleaning or sanitizing fluid 984*b* is caused to overflow into skirt 410 of mixing device 400 by pulsing the whipper 409 and/or modifying the flowrate in flowpath 1260. As a result, cleaning or sanitizing fluid 984*b* that has overflown mixing bowl 406 into skirt 410 drains through flowpath 1240 back into CIP reservoir 980. Additionally, cleaning or sanitizing fluid 984*b* also flows through whipper 409, nozzle 500 (in its cleaning and/or sanitizing position) while traversing flowpath 1250 back to CIP reservoir 980 to be recycled or drained. While this operation is ongoing, pinch actuator 267 is pressing pinching member 261 against pinch block 262 with a preselected force thereby holding hose 212 shut.

Example VII-C

Circulation Cleaning Loop for Milk Manifold

Figure 19:
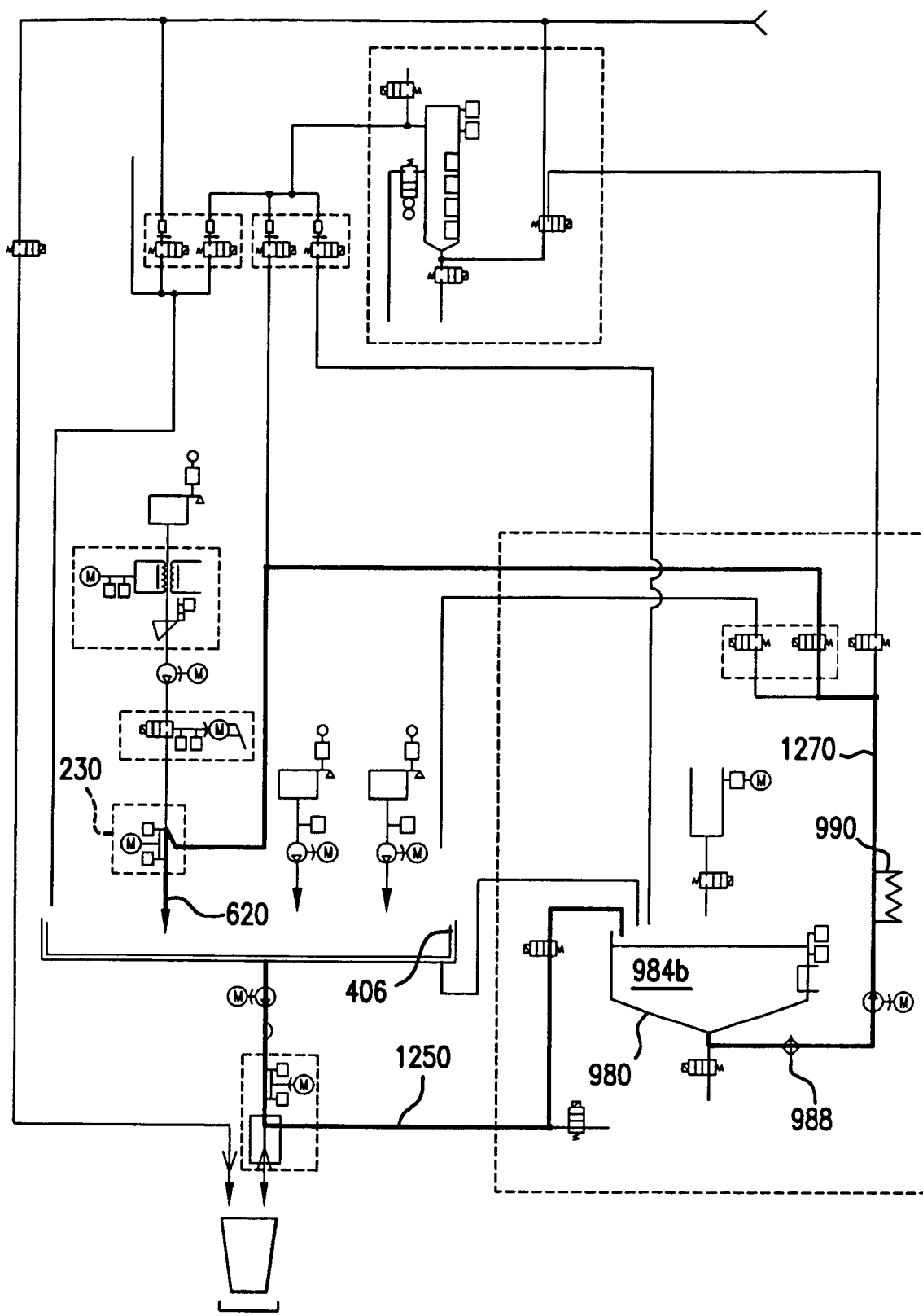
FIG. 19 is a schematic representation of the automated food product dispenser of FIG. 1 showing flowpaths that are active during a daily circulation cleaning loop operation for additionally cleaning the milk manifold.

FIG. 19 shows an additional exemplary embodiment wherein flowpaths 1250 and 1270 are established on a daily basis as a recirculation cleaning loop for milk manifold 230. As embodied herein, flowpath 1270 is established by CIP pump 988 being turned on along with CIP resistive heaters 990. This causes the cleaning or sanitizing fluid 984*b* in CIP reservoir 980 to become heated and flow through flowpath 1270 into milk manifold 230. After flowing through milk manifold 230, cleaning or sanitizing fluid 984*b* flows through dispensing line 620 into mixing bowl 406. The cleaning or sanitizing fluid 984*b* then flows through whipper 409 and flowpath 1250 back to CIP reservoir 980 to be recycled or drained. While this operation is ongoing, pinch actuator 267 is pressing pinching member 261 against pinch block 262 with a preselected force thereby holding hose 212 shut with a preselected pressure to prevent hot water 820 from contaminating milk based fluid 211*a* in reservoir 211.

Example VII-D

CIP Reservoir Filling

Figure 20:
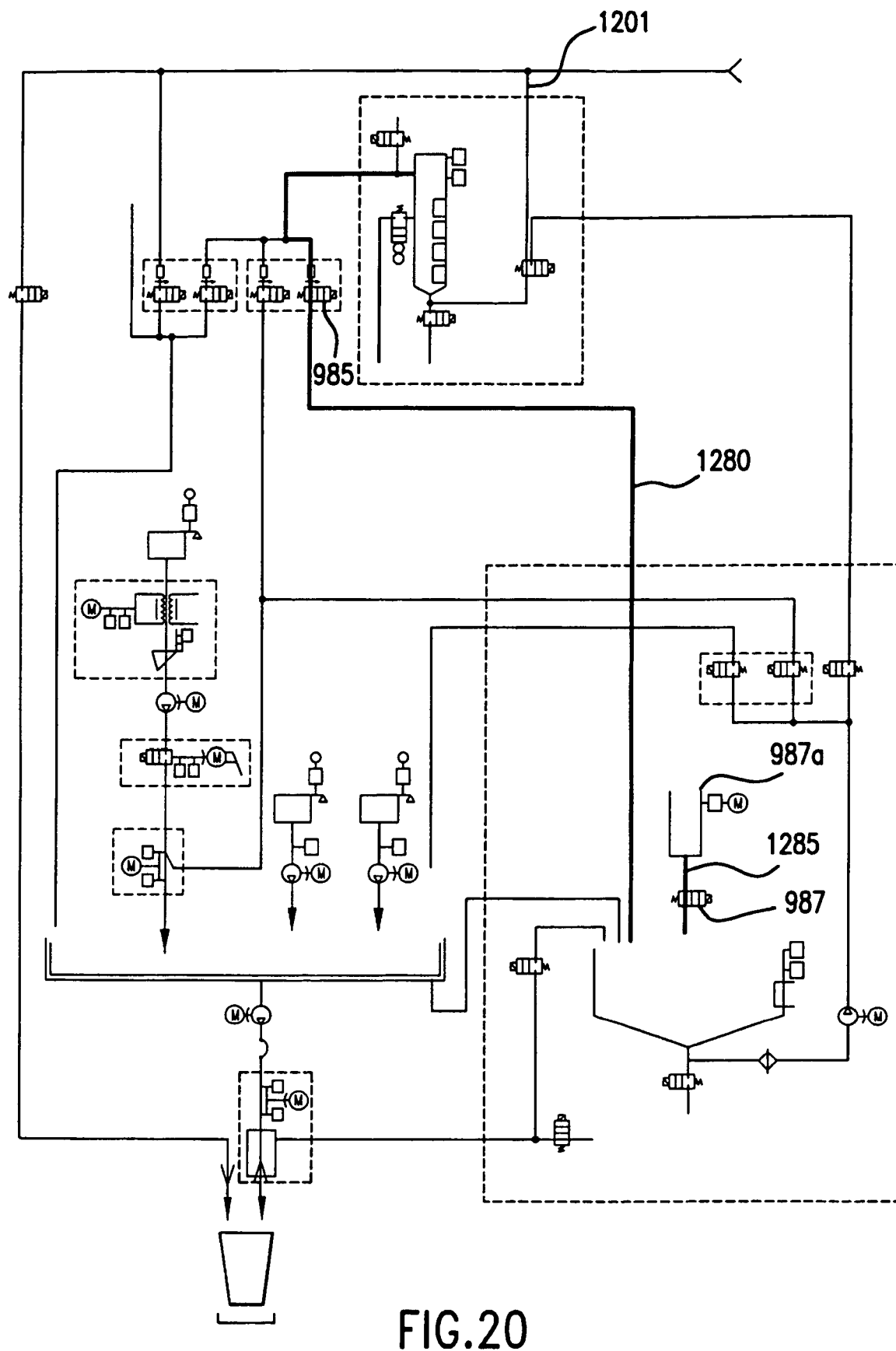
FIG. 20 is a schematic representation of the automated food product dispenser of FIG. 1 showing flowpaths that are active during a daily CIP reservoir filling operation.

FIG. 20 shows an additional exemplary embodiment wherein flowpaths 1280 and 1285 are established on a daily basis to fill CIP reservoir 980. As embodied herein, flowpath 1280 is established between hot water supply module 1201 and CIP reservoir 980 to fill the reservoir by opening CIP hot water valve 985. Flowpath 1285 is established by opening caustic valve 987 to cause cleaning concentrate 987*b* to flow from container 987*a*. Preferably, containers 986*a* and 987*a* are removable and can be replaced by the operator when necessary. Valves 987*b* and 985 are closed when predetermined amounts of cleaning concentrate and hot water, respectively, flow into CIP reservoir 980. While this operation is ongoing, pinch actuator 267 is pressing pinching member 261 against pinch block 262 with a preselected force thereby holding hose 212 shut.

Example VII-E

Milk Manifold Rinse During Inactivity

Figure 21:
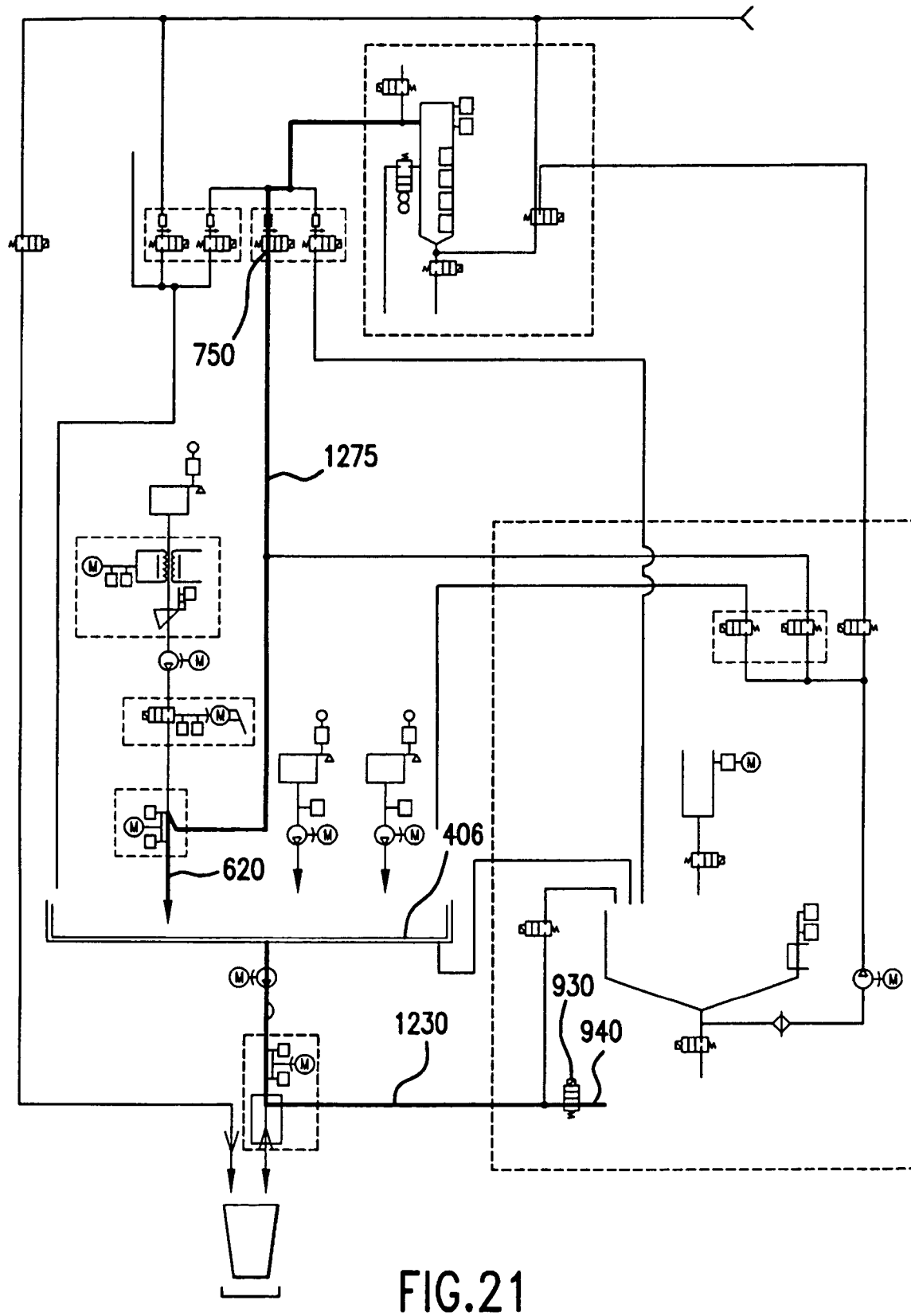
FIG. 21 is a schematic representation of the automated food product dispenser of FIG. 1 showing flowpaths that are active during a milk manifold rinse operation during inactivity.

FIG. 21 shows an additional exemplary embodiment wherein flowpaths 1230 and 1275 are established to rinse milk manifold 230 during inactivity of dispenser 100. As embodied herein, flowpath 1275 is established between hot water supply module 1201 and milk manifold 230 by opening hot water bypass valve 750. Hot water 820 then flows through flowpath 1275 passing through milk manifold 230 and dispensing line 620 into mixing bowl 406. After flowing into mixing bowl 406, hot water 820 then flows through nozzle 500 (in cleaning and/or sanitizing position) through flowpath 1230 and out drain 940 via drain valve 930. While this operation is ongoing, pinch actuator 267 is pressing pinching member 261 against pinch block 262 with a preselected force thereby holding hose 212 shut with a preselected pressure to prevent hot water 820 from contaminating milk based fluid 211*a* in reservoir 211.

Example VII-F

Post Drink Rinse

FIG. 14 shows an additional exemplary embodiment wherein flowpaths 1290 and 1230 are established after each drink is dispensed to flush mixing bowl 406 and dispensing nozzle 500. As embodied herein, flowpath 1290 is established between hot water tank 751 of hot water supply module 1201 and mixing bowl 406 by opening hot water supply valve 950. This causes hot water 820 to flow into mixing bowl 406. Whipper 409 is run on low speed in this example as the hot water 820 traverses flowpath 1230 through the whipper 409 and out drain 940 via drain valve 930.

Example VIII

Sample Operational Regimen

In accordance with the invention, a sample cleaning regimen can be provided as indicated in Table I below:

TABLE I

CIP PROCESS SEQUENCE

| TIME | | STEP | | | |
|---|---|---|---|---|---|
| Hour | STAGE | # | SCREEN | DURATION | DESCRIPTION |
| 0 | 0:00 Pre-Rinse | 1 | Prerinse Delay | 30 s | Time to apply additional pressure to milk tubing pinch valve 260 |
| | 0:30 | 2 | Pre-Rinse | 60 s | HW Tank - Milk Manifold - Mixing Bowl - CIP Nozzle - CIP Tank |
| 1 | | | | | |
| | 1:30 | 3 | First Rinse | 60 s | HW Tank - Milk Manifold - Mixing Bowl - CIP Nozzle - CIP Tank |
| 2 | | | | | |
| | 2:30 | 4 | Fill Tank | 115 s | Fill CIP Tank 980 with water until level sensor activates caustic addition |
| 3 | | | | | |
| 4 | 4:25 Caustic | 5 | Add Caustic | 30 s | Caustic solution added from bottle to CIP Reservoir 980 |
| | 4:55 | 6 | Circ to Milk | 120 s | CIP Tank - CIP Pump - Milk Manifold - Mixing Bowl - CIP Nozzle - CIP Tank |
| 5 | | | | | |
| 6 | | | | | |
| | 6:55 | 7 | Circ to Bowl | 120 s | CIP Tank - CIP Pump - Mixing Bowl - CIP Nozzle - CIP Tank |
| 7 | | | | | |
| 8 | | | | | |
| | 8:55 | 8 | Drain | 30 s | Drain CIP Reservoir |
| 9 | 9:25 Rinse | 9 | Milk Rinse | 120 s | HW Tank - Milk Manifold - Mixing Bowl - CIP Nozzle - Drain |
| 10 | | | | | |
| 11 | 11:25 | 10 | Bowl Rinse | 60 | HW Tank - Mixing Bowl - CIP Nozzle - Drain |
| 12 | 12:25 | 11 | Drain | 30 | Drain flowpath, remove pressure from milk tubing pinch valve |
| | 12:55 | | Off | | |

As seen in Table I above, different regimens are provided for performing different operations with dispenser 100. Instructions for performing these functions at the above specified intervals are preferably written into a computer program in machine readable format for controlling the dispenser 100.

As can be seen, the present invention, as described above and shown in the drawings, provides for more sanitary operation and greater ease of use than with prior art devices.

It will be apparent to those skilled in the art that various modifications and variations can be made in the present system without departing from the spirit or scope of the invention. Thus, it is intended that the present invention include all such modifications and variations within the scope of the appended claims and their equivalents.

What is claimed is:

1. An automated food product dispenser comprising:
   a housing;
   an interface connection configured to receive a supply of a milk based fluid from a milk based fluid reservoir;
   a mixing device configured to receive the milk based fluid and prepare a milk based product;
   a nozzle in fluid association with the mixing device to dispense the milk based product,
   a milk-based flowpath configured to direct the milk based fluid to flow from the interface connection through the mixing device to the nozzle and a product flowpath configured to direct the milk based product to flow from the mixing device to the nozzle, and
   a clean-in-place flowpath assembly physically located within the dispenser housing and including a supply of cleaning or sanitizing fluid and a flowpath which is configured to deliver the cleaning or sanitizing fluid to or through the milk based fluid and product flowpaths.

2. The automated food product dispenser of claim 1, wherein the supply of cleaning or sanitizing fluid is produced within the dispenser by mixing a chemical cleaning concentrate, supplied from a concentrate supply, with water supplied from a water supply to generate a chemical cleaning agent for use as the cleaning or sanitizing fluid.

3. The automated food product dispenser of claim 1, further comprising a central controller including a timer to control a full cleaning-in-place process.

4. The automated food product dispenser of claim 3, further comprising a control panel, wherein the central controller is programmed to run the full cleaning-in-place process in response to user demand.

5. The automated food product dispenser of claim 3, wherein the central controller is programmed to automatically run a time-controlled delivery of one cleaning cycle of chemical cleaning agent through the product flowpath or at least one sanitizing cycle of heated fluid through the product flowpath.

6. The automated food product dispenser of claim 5, wherein the controller is programmed to provide a pre-rinsing cycle in the full cleaning-in-place process that takes place just before the cleaning cycle.

7. The automated food product dispenser of claim 1, which is intended for operation at room temperature and which does not include a refrigeration or freezing unit associated with the milk based fluid reservoir.

8. An automated food product dispenser comprising:
an interface connection configured to receive a supply of a milk based fluid from a milk based fluid reservoir;
a mixing device configured to receive the milk based fluid and prepare a milk based product;
a nozzle in fluid association with the mixing device to dispense the milk based product,
a product flowpath configured to direct the milk based product to flow from the interface connection through the mixing device to the nozzle, and
a clean-in-place flowpath assembly located in the dispenser and including a supply of cleaning or sanitizing fluid and a flowpath which is configured to deliver the cleaning or sanitizing fluid to or through the product flowpath,
wherein the clean-in-place flowpath assembly further includes a buffer reservoir configured to receive a buffer volume of the cleaning or sanitizing fluid, and a line associated with the reservoir and configured to direct the fluid from the buffer reservoir through the product flowpath, wherein the fluid cleans the product flowpath through which it flows.

9. An automated food product dispenser comprising:
an interface connection configured to receive a supply of a milk based fluid from a milk based fluid reservoir;
a mixing device configured to receive the milk based fluid and prepare a milk based product;
a nozzle in fluid association with the mixing device to dispense the milk based product,
a product flowpath configured to direct the milk based product to flow from the interface connection through the mixing device to the nozzle,
a clean-in-place flowpath assembly located in the dispenser and including a supply of cleaning or sanitizing fluid and a flowpath which is configured to deliver the cleaning or sanitizing fluid to or through the product flowpath, and
a water supply for producing the cleaning or sanitizing fluid.

10. An automated food product dispenser comprising:
an interface connection configured to receive a supply of a milk based fluid from a milk based fluid reservoir;
a mixing device configured to receive the milk based fluid and prepare a milk based product;
a nozzle in fluid association with the mixing device to dispense the milk based product,
a product flowpath configured to direct the milk based product to flow from the interface connection through the mixing device to the nozzle, and
a clean-in-place flowpath assembly located in the dispenser and including a supply of cleaning or sanitizing fluid and a flowpath which is configured to deliver the cleaning or sanitizing fluid to or through the product flowpath,
further comprising a removable container that contains the source of chemical cleaning concentrate and is connected in the clean-in-place flowpath assembly to a shut-off valve that is controlled by the controller to deliver and, to optionally meter, an amount of cleaning concentrate to the product flowpath.

11. An automated food product dispenser comprising:
an interface connection configured to receive a supply of a milk based fluid from a milk based fluid reservoir;
a mixing device configured to receive the milk based fluid and prepare a milk based product;
a nozzle in fluid association with the mixing device to dispense the milk based product,
a product flowpath configured to direct the milk based product to flow from the interface connection through the mixing device to the nozzle, and
a clean-in-place flowpath assembly located in the dispenser and including a supply of cleaning or sanitizing fluid and a flowpath which is configured to deliver the cleaning or sanitizing fluid to or through the product flowpath,
wherein the interface connection is adapted to engage the milk based fluid reservoir wherein the milk based fluid reservoir includes a flexible hose portion and a fitment; the interface connection including a fluid chamber having a cleaning or sanitizing fluid inlet that allows the cleaning or sanitizing fluid to enter the fluid chamber, a product inlet for the milk based fluid to enter the fluid chamber and a product outlet for a milk based product to exit the fluid chamber to the product flowpath; and connection means at the product inlet configured for hygienically and removably connecting the fitment of the milk based fluid reservoir to the fluid chamber.

12. The automated food product dispenser of claim 11, which further comprises a valve adapted to be controlled by the controller to operatively engage the flexible hose portion to selectively block flow of the milk based fluid at a closing point.

13. The automated food product dispenser of claim 11, which further comprises projection means for promoting cleaning of the fitment and flexible hose portion up to the closing point.

14. An automated food product dispenser comprising:
an interface connection configured to receive a supply of a milk based fluid from a milk based fluid reservoir;
a mixing device configured to receive the milk based fluid and prepare a milk based product;
a nozzle in fluid association with the mixing device to dispense the milk based product,
a product flowpath configured to direct the milk based product to flow from the interface connection through the mixing device to the nozzle, and
a clean-in-place flowpath assembly located in the dispenser and including a supply of cleaning or sanitizing fluid and a flowpath which is configured to deliver the cleaning or sanitizing fluid to or through the product flowpath, wherein the mixing device includes a mixing bowl configured to collect the milk based fluid, water and other beverage forming components; and a mixer to mix the milk based fluid, water and other beverage forming components together to form the milk based product.

15. The automated food product dispenser of claim 14, wherein the clean-in-place flowpath assembly further includes a mixing bowl feed line for directly directing cleaning or sanitizing fluid to the mixing bowl to clean the mixing bowl and the product flowpath that is arranged downstream of the mixing bowl.

16. The automated food product dispenser of claim 15, the clean-in-place flowpath assembly further includes one or more valves controlled by the controller to selectively open or close either the mixing bowl feed line or a portion of the product flowpath.

17. The automated food product dispenser of claim 14, wherein the mixing bowl further includes an outer skirt that surrounds the mixing bowl and a fluid outlet connected to a downstream cleaning fluid evacuation conduit of the clean-in-place flowpath assembly, wherein the outer skirt is configured in a manner to collect fluid that overflows the bowl, and wherein the downstream cleaning fluid evacuation conduit is configured to selectively direct the collected fluid to the buffer reservoir to recirculate the cleaning or sanitizing fluid, or to the drain.

18. The automated food product dispenser of claim 14, wherein the mixer can be controlled to:

run intermittently to assist in making the cleaning fluid overflow the mixing bowl when the whipper is in a turn-off mode and, to assist in driving the cleaning or sanitizing fluid through the bowl and product flowpath to the nozzle when the whipper is in a turn-on mode.

19. An automated food product dispenser comprising:

an interface connection configured to receive a supply of a milk based fluid from a milk based fluid reservoir;

a mixing device configured to receive the milk based fluid and prepare a milk based product;

a nozzle in fluid association with the mixing device to dispense the milk based product, a product flowpath configured to direct the milk based product to flow from the interface connection through the mixing device to the nozzle, and a clean-in-place flowpath assembly located in the dispenser and including a supply of cleaning or sanitizing fluid and a flowpath which is configured to deliver the cleaning or sanitizing fluid to or through the product flowpath, wherein the nozzle is controlled by the controller to be positioned in either:

a dispensing position wherein the milk based product is dispensed to a dispensing zone, or a cleaning position wherein the nozzle recirculates cleaning or sanitizing fluid or drains cleaning fluid from the mixing bowl.

20. An automated food product dispenser comprising:

an interface connection configured to receive a supply of a milk based fluid from a milk based fluid reservoir;

a mixing device configured to receive the milk based fluid and prepare a milk based product;

a nozzle in fluid association with the mixing device to dispense the milk based product, a product flowpath configured to direct the milk based product to flow from the interface connection through the mixing device to the nozzle, and a clean-in-place flowpath assembly located in the dispenser and including a supply of cleaning or sanitizing fluid and a flowpath which is configured to deliver the cleaning or sanitizing fluid to or through the product flowpath, wherein the interface connection comprises a fluid chamber that includes a cleaning fluid inlet for allowing the cleaning fluid to enter the chamber, a product inlet for the milk based fluid to enter the chamber and a product outlet for the product to exit the chamber to the product flow path.

* * * * *

UNITED STATES PATENT AND TRADEMARK OFFICE
CERTIFICATE OF CORRECTION

PATENT NO. : 7,325,485 B2 Page 1 of 1
APPLICATION NO. : 11/033867
DATED : February 5, 2008
INVENTOR(S) : Carhuff et al.

It is certified that error appears in the above-identified patent and that said Letters Patent is hereby corrected as shown below:

Title Page:
Item (56) References Cited, OTHER PUBLICATIONS, insert the following reference:
-- Excerpts from User Manual of "Bremer Viva Au Lait" Beverage Dispenser --.

Column 31:
Line 15 (claim 16, line 1), after "claim 15," insert -- wherein --.

Signed and Sealed this

Thirteenth Day of May, 2008

JON W. DUDAS
*Director of the United States Patent and Trademark Office*